(12) United States Patent
Kapeller-Libermann

(10) Patent No.: US 6,620,592 B2
(45) Date of Patent: Sep. 16, 2003

(54) 18036, A NOVEL CALPAIN-LIKE PROTEASE AND USES THEREOF

(75) Inventor: Rosana Kapeller-Libermann, Chestnut Hill, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/794,960

(22) Filed: Feb. 26, 2001

(65) Prior Publication Data

US 2002/0009774 A1 Jan. 24, 2002

Related U.S. Application Data

(60) Provisional application No. 60/185,333, filed on Feb. 28, 2000.

(51) Int. Cl.[7] ............................ C12N 9/50; C12N 5/10; C12N 1/21; C12Q 1/37; C12P 21/00
(52) U.S. Cl. ..................... 435/23; 435/219; 435/69.1; 435/325; 435/320.1; 435/252.3; 536/23.2
(58) Field of Search ..................... 435/23, 69.1, 219, 435/325, 252.3, 320.1, 226; 536/23.2

(56) References Cited

U.S. PATENT DOCUMENTS

| | | | |
|---|---|---|---|
| 5,545,672 A | | 8/1996 | Knutson |
| 6,235,481 B1 | * | 5/2001 | Horikawa et al. ............. 435/6 |

FOREIGN PATENT DOCUMENTS

| | | |
|---|---|---|
| EP | 1 130 094 A2 | 9/2001 |
| WO | WO00/09709 A2 | 2/2000 |
| WO | WO00/23603 A2 | 4/2000 |

OTHER PUBLICATIONS

Horikawa, Y., et al., "Genetic Variation in the Gene Encoding Calpain–10 is Associated with Type 2 Diabetes Mellitus," *Nature Genetics*, Oct. 2000, pp. 163–175, vol. 26, No. 2.

EMBL Database Report for Accession No. Q9WVF0, Nov. 1, 1999 (XP–002139084).

GenBank Report for Accession No. AA514377, Direct Submission 1997.

GenBank Report for Accession No. AF089088, Direct Submission Sep. 2, 1998.

GenBank Report for Accession No. AF089089, Direct Submission Sep. 2, 1998.

GenBank Report for Accession No. AF089090, Direct Submission Sep. 2, 1998.

GenBank Report for Accession No. AF089091, Direct Submission Sep. 2, 1998.

GenBank Report for Accession No. AF089092, Direct Submission Sep. 2, 1998.

GenBank Report for Accession No. AF089093, Direct Submission Sep. 2, 1998.

GenBank Report for Accession No. AF089094, Direct Submission Sep. 2, 1998.

GenBank Report for Accession No. AF126867, Direct Submission Feb. 9, 1999.

GenBank Report for Accession No. AI024530, Direct Submission 1997.

GenBank Report for Accession No. AI038601, Direct Submission 1997.

GenBank Report for Accession No. AI652032, Direct Submission 1997.

GenBank Report for Accession No. AI675939, Direct Submission 1997.

GenBank Report for Accession No. AI685426, Direct Submission 1997.

GenBank Report for Accession No. BE046198, Direct Submission 1997.

GenBank Report for Accession No. BE293992, Direct Submission 1999.

GenBank Report for Accession No. BE312136, Direct Submission 1999.

GenBank Report for Accession No. BG231622, Direct Submission 1997.

* cited by examiner

*Primary Examiner*—Rebecca E. Prouty
(74) *Attorney, Agent, or Firm*—Millennium Pharmaceuticals, Inc.

(57) ABSTRACT

Novel calpain-like protease polypeptides, proteins, and nucleic acid molecules are disclosed. In addition to isolated, full-length calpain-like protease proteins, the invention further provides isolated calpain-like protease fusion proteins, antigenic peptides, and anti-calpain-like protease antibodies. The invention also provides calpain-like protease nucleic acid molecules, recombinant expression vectors containing a nucleic acid molecule of the invention, host cells into which the expression vectors have been introduced, and nonhuman transgenic animals in which a calpain-like protease gene has been introduced or disrupted. Diagnostic, screening, and therapeutic methods utilizing compositions of the invention are also provided.

18 Claims, 10 Drawing Sheets

Input file fbh38647F1; Output File 38647.trans
Sequence length 2180

ACGCGTCCGAGCGGGCCGGCGTACTGGCCTGGTCCAGCACCTGCGGGGCCCTCGGGCTTGGAGGGCTGGGCCGGGCGGG

GAACGGGCGGGGCGGGCCGGAGGCGGCGGCGGCTGACTCGCCTTCTCTCCGGGGCTGCACCCCGAGGCAACCGGCTGC

```
                                   M   R   A   G   R   G   A   T   P   A   R   E   L      13
AGATGGGAGCCCGCGGAGCCGAGG ATG CGG GCG GGC CGG GGC GCG ACG CCG GCG AGG GAG CTG          39
 F   R   D   A   A   F   P   A   A   D   S   S   L   F   C   D   L   S   T   P        33
TTC CGG GAC GCC GCC TTC CCC GCC GCG GAC TCC TCG CTC TTC TGC GAC TTG TCT ACG CCG         99
 L   A   Q   F   R   E   D   I   T   W   R   R   P   Q   E   I   C   A   T   P        53
CTG GCC CAG TTC CGC GAG GAC ATC ACG TGG AGG CGG CCC CAG GAG ATT TGT GCC ACA CCC        159
 R   L   F   P   D   D   P   R   E   G   Q   V   K   Q   G   L   L   G   D   C        73
CGG CTG TTT CCA GAT GAC CCA CGG GAA GGG CAG GTG AAG CAG GGG CTG CTG GGG GAT TGC        219
 W   F   L   C   A   C   A   A   L   Q   K   S   R   H   L   L   D   Q   V   I        93
TGG TTC CTG TGT GCC TGC GCC GCG CTG CAG AAG AGC AGG CAC CTC CTG GAC CAG GTC ATT        279
 P   P   G   Q   P   S   W   A   D   Q   E   Y   R   G   S   F   T   C   R   I       113
CCT CCG GGA CAG CCG AGC TGG GCC GAC CAG GAG TAC CGG GGC TCC TTC ACC TGT CGC ATT        339
 W   Q   F   G   R   W   V   E   V   T   T   D   D   R   L   P   C   L   A   G       133
TGG CAG TTT GGA CGC TGG GTG GAG GTC ACC ACA GAT GAC CGC CTG CCG TGC CTT GCA GGG        399
 R   L   C   F   S   R   C   Q   R   E   D   V   F   W   L   P   L   L   E   K       153
AGA CTC TGT TTC TCC CGC TGC CAG AGG GAG GAT GTG TTC TGG CTC CCC TTA CTG GAA AAG        459
 V   Y   A   K   V   H   G   S   Y   E   H   L   W   A   G   Q   V   A   D   A       173
GTC TAC GCC AAG GTC CAT GGG TCC TAC GAG CAC CTG TGG GCC GGG CAG GTG GCG GAT GCC        519
 L   V   D   L   T   G   G   L   A   E   R   W   N   L   K   G   V   A   G   S       193
CTG GTG GAC CTG ACC GGC GGC CTG GCA GAA AGA TGG AAC CTG AAG GGC GTA GCA GGA AGC        579
 G   G   Q   Q   D   R   P   G   R   W   E   H   R   T   C   R   Q   L   L   H       213
GGA GGC CAG CAG GAC AGG CCA GGC CGC TGG GAG CAC AGG ACT TGT CGG CAG CTG CTC CAC        639
 L   K   D   Q   C   L   I   S   C   C   V   L   S   P   R   A   G   A   R   E       233
CTG AAG GAC CAG TGT CTG ATC AGC TGC TGC GTG CTC AGC CCC AGA GCA GGT GCC CGG GAG        699
 L   G   E   F   H   A   F   I   V   S   D   L   R   E   L   Q   G   Q   A   G       253
CTG GGG GAG TTC CAT GCC TTC ATT GTC TCG GAC CTG CGG GAG CTC CAG GGT CAG GCG GGC        759
 Q   C   I   L   L   L   R   I   Q   N   P   W   G   R   R   C   W   Q   G   L       273
CAG TGC ATC CTG CTG CTG CGG ATC CAG AAC CCC TGG GGC CGG CGG TGC TGG CAG GGG CTC        819
 W   R   E   G   G   E   G   W   S   Q   V   D   A   A   V   A   S   E   L   L       293
TGG AGA GAG GGG GGT GAA GGG TGG AGC CAG GTA GAT GCA GCG GTA GCA TCT GAG CTC CTG        879
 S   Q   L   Q   E   G   E   F   W   V   E   E   E   E   F   L   R   E   F   D       313
TCC CAG CTC CAG GAA GGG GAG TTC TGG GTG GAG GAG GAG GAG TTC CTC AGG GAG TTT GAC        939
 E   L   T   V   G   Y   P   V   T   E   A   G   H   L   Q   S   L   Y   T   E       333
GAG CTC ACC GTT GGC TAC CCG GTC ACG GAG GCC GGC CAC CTG CAG AGC CTC TAC ACA GAG        999
 R   L   L   C   H   T   R   A   L   P   G   A   W   V   K   G   Q   S   A   G       353
AGG CTG CTC TGC CAT ACG CGG GCG CTG CCT GGG GCC TGG GTC AAG GGC CAG TCA GCA GGA       1059
```

FIG. 1A.

```
  G   C   R   N   N   S   G   F   P   S   N   P   K   F   W   L   R   V   S   E   373
GGC TGC CGG AAC AAC AGC GGC TTT CCC AGC AAC CCC AAA TTC TGG CTG CGG GTC TCA GAA 1119
  P   S   E   V   Y   I   A   V   L   Q   R   S   R   L   H   A   A   D   W   A   393
CCG AGT GAG GTG TAC ATT GCC GTC CTG CAG AGA TCC AGG CTG CAC GCG GCG GAC TGG GCA 1179
  G   R   A   R   A   L   V   G   D   S   H   T   S   W   S   P   A   S   I   P   413
GGC CGG GCC CGG GCA CTG GTG GGT GAC AGT CAT ACT TCG TGG AGC CCA GCG AGC ATC CCG 1239
  G   K   H   Y   Q   A   V   G   L   H   L   W   K   V   P   E   G   G   R   S   433
GGC AAG CAC TAC CAG GCT GTG GGT CTG CAC CTC TGG AAG GTC CCA GAG GGT GGA AGG AGC 1299
  Q   D   A   P   P   L   L   L   Q   E   P   L   L   S   C   V   P   H   R   Y   453
CAG GAC GCA CCC CCA CTG CTG CTG CAG GAG CCG CTG CTG AGC TGC GTG CCA CAT CGC TAC 1359
  A   Q   E   V   S   R   L   C   L   L   P   A   G   T   Y   K   V   V   P   S   473
GCC CAG GAG GTG AGC CGG CTC TGC CTC CTG CCT GCG GGC ACC TAC AAG GTT GTG CCC TCC 1419
  T   Y   L   P   D   T   E   G   A   F   T   V   T   I   A   T   R   I   D   R   493
ACC TAC CTG CCG GAC ACA GAG GGG GCC TTC ACA GTG ACC ATC GCA ACC AGG ATT GAC AGG 1479
  P   S   I   H   S   Q   E   M   L   G   Q   F   L   Q   E   V   S   V   M   A   513
CCA TCC ATT CAC AGC CAG GAG ATG CTG GGC CAG TTC CTC CAA GAG GTC TCC GTC ATG GCA 1539
  V   M   K   T   *                                                                 518
GTG ATG AAA ACC TAA                                                               1554
```

CAGGGTGGCCCCCTGTGCCAGCTCAGGTGACTGGAGCCCGAGGGCCTGACAGGTTCCCAGCAGCTGGGCCGGCCAGCCT

TGCACTGTGGGGGCTGGTCCTGAGTCTTGGCCTGCCTCCCAGCCCTGCCAGGGGGCTGCGGCCTAGGGGTCCACGGGAA

GCCTCCGTCAGGAGAGACGCAGCCCTGGGGGCCAGCTGGTGCTGCAAGGAAGGGTGGGAAGCTTGCTGGCTTCTGTTGC

GCCACTGAGACGGCAGAGACCCCAGGATCCCAGAGCTTCCCAGGATCCCTCCCAGATCCTCTGCTGACTCCATATGGAG

GCCTCACACCCAGAGGGTAGGGCAGCAGATCTTCTTTATAACTATTTATTGTTCGAATCACTTTTAGGATGTAACTTTA

TAAATAAACATGAGCGCTGATGATTTGCAAAAAAAAAAAAAAAAAAAAAA

FIG. 1B.

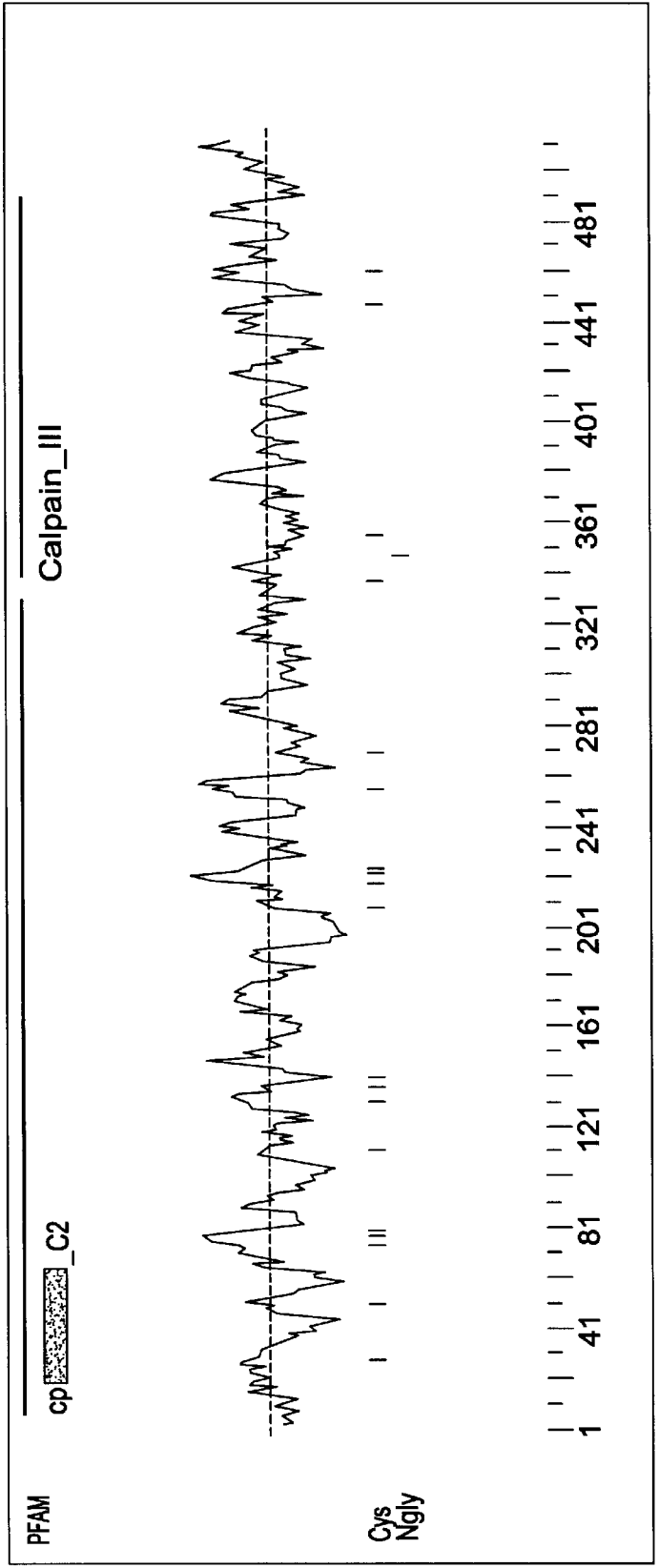

FIG. 3.

>38647
MRAGRGATPARELFRDAAFPAADSSLFCDLSTPLAQFREDITWRRPQEICATPRLFPDDP
REGGQVKQGLLGDCWFLCACAALQKSRHLLDQVIPPGQPSWADQEYRGSFTCRIWQFGRWV
EVTTDDRLPCLAGRLCFSRCQREDVFWLPLLEKVYAKVHGSYEHLWAGQVADALVDLTGG
LAERWNLKGVAGSGGQDRPGRWEHRTCRQLLHLKDQCLISCCVLSPRAGARELGEFHAF
IVSDLRELQGGQAGQCILLLRIQNPWGRRCWQGLWREGGEGWSQVDAAVASELLSQLQEGE
FWVEEEEFLREFDELTVGYPVTEAGHLQSLYTERLLCHTRALPGAWVKGQSAGGCRNNSG
FPSNPKFWLRVSEPSEVYIAVLQRSRLHAADWAGRARALVGDSHTSWSPASIPGKHYQAV
GLHLWKVPEGGRSQDAPPLLLQEPLLSCVPHRYAQEVSRLCLLPAGTYKVVPSTYLPDTE
GAFTVTIATRIDRPSIHSQEMLGQFLQEVSVMAVMKT

Prosite Pattern Matches for 38647

Prosite version: Release 12.2 of February 1995

>PS00001/PDOC00001/ASN_GLYCOSYLATION N-glycosylation site.

Query: 357    NNSG    360

>PS00005/PDOC00005/PKC_PHOSPHO_SITE Protein kinase C phosphorylation site.

Query: 42    TWR    44
Query: 52    TPR    54
Query: 110   TCR    112
Query: 207   TCR    209
Query: 226   SPR    228
Query: 332   TER    334
Query: 467   TYK    469

>PS00006/PDOC00006/CK2_PHOSPHO_SITE Casein kinase II phosphorylation site.

Query: 99    SWAD    102
Query: 123   TTDD    126
Query: 282   SQVD    285
Query: 489   TRID    492

>PS00008/PDOC00008/MYRISTYL N-myristoylation site.

Query: 6     GATPAR    11
Query: 107   GSFTCR    112
Query: 189   GVAGSG    194
Query: 349   GQSAGG    354

>PS00009/PDOC00009/AMIDATION Aidation site.

Query: 265   WGRR    268

>PS00139/PDOC00126/THIOL_PROTEASE_CYS Eukaryotic thiol (cysteine) proteases cysteine active site.

Query: 67    QGLLGDCWFLCA    78

FIG. 4.

PSORT Prediction of Protein Localization

MITDISC: discrimination of mitochondrial targeting seq
    R content:        4         Hyd Moment (75):  4.34
    Hyd Moment (95): 10.93    G content:       2
    D/E content:     2         S/T content:     1
    Score:  -3.73

Gavel: prediction of cleavage sites for mitochondrial preseq
    R-2 motif at 15 GRG/AT NUCDISC: discrimination of nuclear localization signals
    pat4:   none
    pat7:   none
    bipartite:  none
    content of basic residues:  10.6%
    NLS Score:  -0.47

ER Membrane Retention Signals:
    XXRR-like motif in the N-terminus: RAGR
    KKXX- like motif in the C-terminus: AVMK Final Results (k = 9/23):

60.9 %: mitochonrial
    21.7 %: nuclear
    13.0 %: cytoplasmic
     4.3 %: peroxisomal prediction for 38647 is mit (k=23)

| Start | End | Feature | Seq |

FIG. 5.

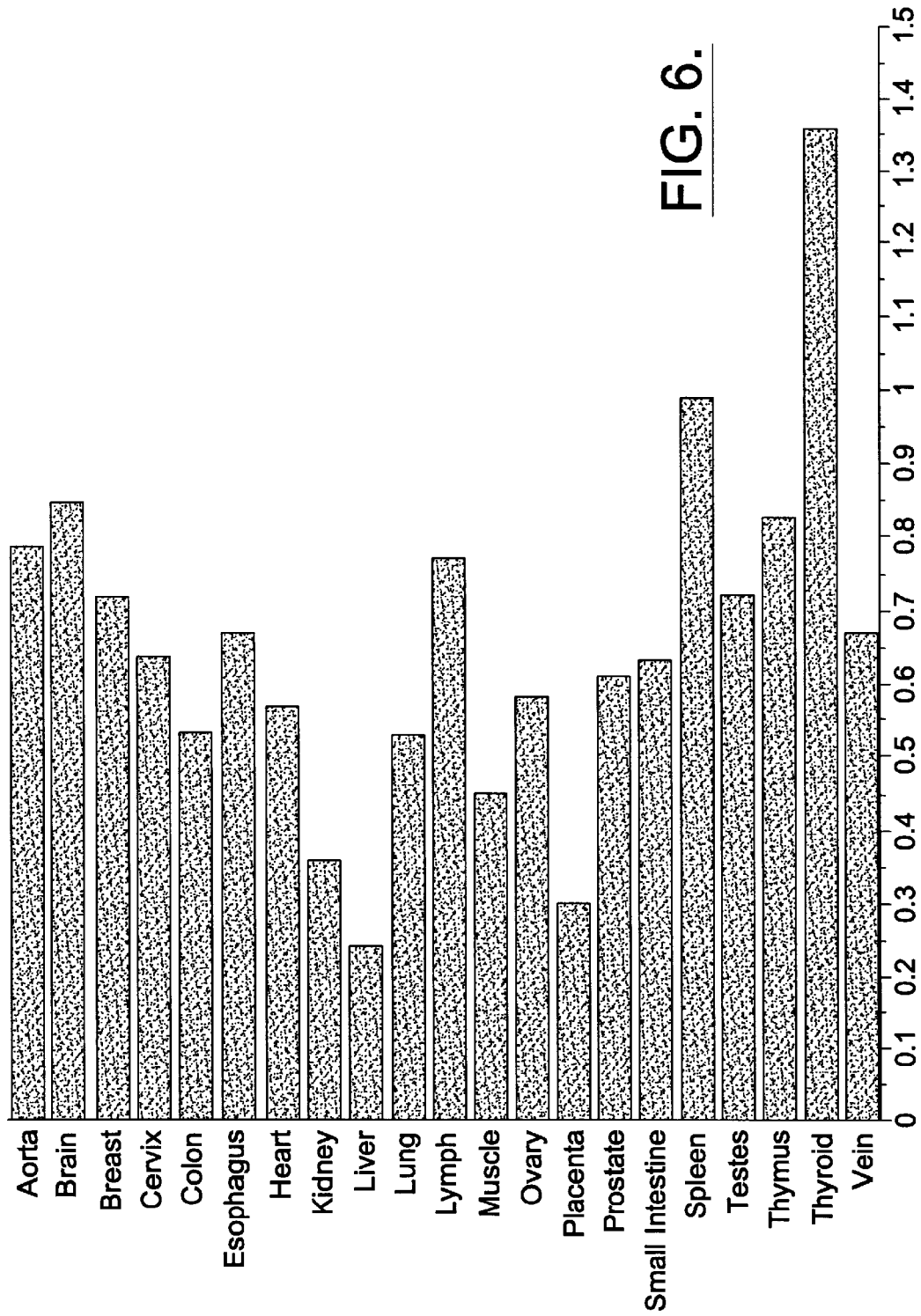

Alignments of top-scoring domains:
Peptidase_C2: domain 1 of 1, from 13 to 322: score 203.2, E = 4e-57

```
              *->LFeDpsFPaapkSLgykplgpassktrgieWkRPhEInenpqAYPPW
                 LF+D +FPaa++SL+    p   +i W+RP EI++ p+
    38647    13  LFRDAAFPAADSSLFCDLSTPLAQFREDITWRRPQEICATPR----- 54

FivgGasRtDIcQGaLGDCWLLAAiAsLt1neeL1krVvPhdq.sfqenW
                 + + +    + QG LGDCW+L A A+L   +L1++V+P +q+s  +
    38647    55  LFPDDPREGQVKQGLLGDCWFLCACAALQKSRHLLDQVIPPGQpSWADQ- 103

RLYRyYaGifhfrfwqyGkWvdVvvDD1LPtkdgkVpiL1fvhsaernEF
                 +Y G f   r+wq+G Wv+V +DD+LP+   q+   L f++        F
    38647   104  ----EYRGSFTCRIWQFGRWVEVTTDDRLPCLAGR---LCFSRCQREDVF 146

WSALLEKAYAK1nGcYEaLYNAiLqisGGsttEA1ed1TGgvcesyeLkk
                 W +LLEK YAK++G+YE+L          G   Al d1TGg +e   Lk
    38647   147  WLPLLEKVYAKVHGSYEHL-------WAGQVADALVDLTGGLAERWNLKG 189 apspmpSetdLnL1niik.kalergsns1LrDsDLvrf111gcsiditsp
                  +    S    +  ++++ ++          L  + 1+ c++ ++
    38647   190  VAG---SGGQQDRPGRWEhRTCRQLL-------HLKDQCLISCCVLSP-- 227 vdmEakmakGLvkgHAYSVTgvkevny.rGekqkLiR1RNPWGdevEWtG
                     a   L   HA  V ++ e + +  G+  +  l+R+ NPWG   W G
    38647   228  ----RAGARELGEFHAFIVSDLRELQGqAGQCILLLRIQNPWG-RRCWQG 272 dWsDsspdWreidedekarlq1kfeeDGeFWmSfeDFlnhFsrlEICn.L
                 W   +    W+ +d      +1+++    +GeFW    e F1++F+ 1 + +++
    38647   273  LWREGGEGWSQVDAAVASELLSQLQ-EGEFWVEEEEFLREFDELTVGYpV 321 t<-*
                 t
    38647   322  T    322
```

FIG. 7.

```
>1154 p99.2 (42) CAN2(4) CAN3(4) CAN(2)   // PROTEASE CALPAIN HYDROLASE SUBUNIT
     NEUTRAL THIOL LARGE CALCIUM-ACTIVATED PROTEINASE CANP
     Length = 327

Score = 401 (146.2 bits), Expect = 1.0e-37, P = 1.0e-37
  Identities = 108/306 (35%), Positives = 151/306 (49%)

Query:   13 LFRDAAFPAADSSL-FCDLSTPLAQFREDITWRRPQEICATP--RLFPDDPREGQVK--- 66
            LF D +FP      SL + +L P + +   + I W+RP EIC+ P       P    G +
Sbjct:    1 LFEDPSFPPNPKSLGYKELG-PNSSKTKGIEWKRPSEICSNPDDHSMPQFIVGGATRTDI 59

Query:   67 -QGL-LGDCWFLCACAALQKSRHLLDQVIPPGQP-SW--ADQEYRGSFTCRIWQFGRWVE 121
             QG  LGDCW L A A+L +  ll +VIP Q  W    + Y G F  R WQ+G WV+
Sbjct:   60 CQGTALGDCWLLAALASLTLNEELLHRVIPHDQSFQWDPRKENYAGIFHFRFWQYGEWVD 119

Query:  122 VTTDDRLPCLAGR--LCFSRCQREDVFWLPLLEKVYAKVHGSYEHLWAGQVADALVDLTG 179
            V  DD LP   G    L F     + FW LLEK YAK+HGSYE L G  ++A D  TG
Sbjct:  120 VVIDDYLPTKNGENSLIFVHSNERNEFWSALLEKAYAKLHGSYEALSGGNTSEAFEDFTG 179

Query:  180 GLAERWNLKGVAGSGGQQ---DRPGRWEHRTCRQLLHLKDQCLISCCVLSPRAGARE--- 233
            G+ E ++L+    S  ++    D   WE     + L+    L+c + + AE
Sbjct:  180 GVCEWYDLQKSTKSMPKEAPSDTDQLWEIL----MKALERGSLMGCSIDTVTSAAEEEAQ 235

Query:  234 ----LGEFHAFIVSDLRELQGQAGQCILLLRIQNPWGRRCWQGLWREGGEGWSQVDAAVA 289
                L + HA+ V+D++E+ + GQ   L+R++NPWG    W G W +     W+ VD
Sbjct:  236 TEQGLVKGHAYSVTDVKEVNYR-GQGHRLIRLRNPWGEVEWNGPWSDNSPEWNSVDKDEK 294

Query:  290 SELLSQ 295
             + SQ
Sbjct:  295 ENMGSQ 300
```

FIG. 8.

```
                         SEQUENCE LISTING

<160> NUMBER OF SEQ ID NOS:  6

<210> SEQ ID NO 1
<211> LENGTH: 2180
<212> TYPE: DNA
<213> ORGANISM: Homo sapiens
<220> FEATURE:
<221> NAME/KEY: CDS
<222> LOCATION: (183)...(1737)

<400> SEQUENCE: 1
acgcgtccga gcgggccggc gtactggcct ggtccagcac ctgcggggcc ctcgggcttg      60
gagggctggg ccgggcgggg aacgggcggg gcgggccgga ggcggcggcg gctgactcgc     120
cttctctccg gggctgcgac cccgaggcaa ccggctgcag atgggagccc gcggagccga     180 gg atg cgg gcg ggc cgg ggc gcg acg ccg gcg agg gag ctg ttc cgg        227
   Met Arg Ala Gly Arg Gly Ala Thr Pro Ala Arg Glu Leu Phe Arg
   1               5                  10                  15 gac gcc gcc ttc ccc gcc gcg gac tcc tcg ctc ttc tgc gac ttg tct       275
Asp Ala Ala Phe Pro Ala Ala Asp Ser Ser Leu Phe Cys Asp Leu Ser
                20                  25                  30 acg ccg ctg gcc cag ttc cgc gag gac atc acg tgg agg cgg ccc cag       323
Thr Pro Leu Ala Gln Phe Arg Glu Asp Ile Thr Trp Arg Arg Pro Gln
            35                  40                  45 gag att tgt gcc aca ccc cgg ctg ttt cca gat gac cca cgg gaa ggg       371
Glu Ile Cys Ala Thr Pro Arg Leu Phe Pro Asp Asp Pro Arg Glu Gly
        50                  55                  60 cag gtg aag cag ggg ctg ctg ggg gat tgc tgg ttc ctg tgt gcc tgc       419
Gln Val Lys Gln Gly Leu Leu Gly Asp Cys Trp Phe Leu Cys Ala Cys
    65                  70                  75 gcc gcg ctg cag aag agc agg cac ctc ctg gac cag gtc att cct ccg       467
Ala Ala Leu Gln Lys Ser Arg His Leu Leu Asp Gln Val Ile Pro Pro
80                  85                  90                  95 gga cag ccg agc tgg gcc gac cag gag tac cgg ggc tcc ttc acc tgt       515
Gly Gln Pro Ser Trp Ala Asp Gln Glu Tyr Arg Gly Ser Phe Thr Cys
                100                 105                 110 cgc att tgg cag ttt gga cgc tgg gtg gag gtg acc aca gat gac cgc       563
Arg Ile Trp Gln Phe Gly Arg Trp Val Glu Val Thr Thr Asp Asp Arg
            115                 120                 125 ctg ccg tgc ctt gca ggg aga ctc tgt ttc tcc cgc tgc cag agg gag       611
Leu Pro Cys Leu Ala Gly Arg Leu Cys Phe Ser Arg Cys Gln Arg Glu
        130                 135                 140 gat gtg ttc tgg ctc ccc tta ctg gaa aag gtc tac gcc aag gtc cat       659
Asp Val Phe Trp Leu Pro Leu Leu Glu Lys Val Tyr Ala Lys Val His
    145                 150                 155 ggg tcc tac gag cac ctg tgg gcc ggg cag gtg gcg gat gcc ctg gtg       707
Gly Ser Tyr Glu His Leu Trp Ala Gly Gln Val Ala Asp Ala Leu Val
160                 165                 170                 175
```

-continued

| | | | | | | | | | | | | | | | | |
|---|---|---|---|---|---|---|---|---|---|---|---|---|---|---|---|---|
| gac | ctg | acc | ggc | ggc | ctg | gca | gaa | aga | tgg | aac | ctg | aag | ggc | gta | gca | 755 |
| Asp | Leu | Thr | Gly | Gly | Leu | Ala | Glu | Arg | Trp | Asn | Leu | Lys | Gly | Val | Ala | |
| | | | 180 | | | | | 185 | | | | | 190 | | | |
| gga | agc | gga | ggc | cag | cag | gac | agg | cca | ggc | cgc | tgg | gag | cac | agg | act | 803 |
| Gly | Ser | Gly | Gly | Gln | Gln | Asp | Arg | Pro | Gly | Arg | Trp | Glu | His | Arg | Thr | |
| | | | 195 | | | | | 200 | | | | | 205 | | | |
| tgt | cgg | cag | ctg | ctc | cac | ctg | aag | gac | cag | tgt | ctg | atc | agc | tgc | tgc | 851 |
| Cys | Arg | Gln | Leu | Leu | His | Leu | Lys | Asp | Gln | Cys | Leu | Ile | Ser | Cys | Cys | |
| | 210 | | | | | 215 | | | | | 220 | | | | | |
| gtg | ctc | agc | ccc | aga | gca | ggt | gcc | cgg | gag | ctg | ggg | gag | ttc | cat | gcc | 899 |
| Val | Leu | Ser | Pro | Arg | Ala | Gly | Ala | Arg | Glu | Leu | Gly | Glu | Phe | His | Ala | |
| | 225 | | | | | 230 | | | | | 235 | | | | | |
| ttc | att | gtc | tcg | gac | ctg | cgg | gag | ctc | cag | ggt | cag | gcg | ggc | cag | tgc | 947 |
| Phe | Ile | Val | Ser | Asp | Leu | Arg | Glu | Leu | Gln | Gly | Gln | Ala | Gly | Gln | Cys | |
| 240 | | | | | 245 | | | | | 250 | | | | | 255 | |
| atc | ctg | ctg | ctg | cgg | atc | cag | aac | ccc | tgg | ggc | cgg | cgg | tgc | tgg | cag | 995 |
| Ile | Leu | Leu | Leu | Arg | Ile | Gln | Asn | Pro | Trp | Gly | Arg | Arg | Cys | Trp | Gln | |
| | | | | 260 | | | | | 265 | | | | | 270 | | |
| ggg | ctc | tgg | aga | gag | ggg | ggt | gaa | ggg | tgg | agc | cag | gta | gat | gca | gcg | 1043 |
| Gly | Leu | Trp | Arg | Glu | Gly | Gly | Glu | Gly | Trp | Ser | Gln | Val | Asp | Ala | Ala | |
| | | 275 | | | | | 280 | | | | | 285 | | | | |
| gta | gca | tct | gag | ctc | ctg | tcc | cag | ctc | cag | gaa | ggg | gag | ttc | tgg | gtg | 1091 |
| Val | Ala | Ser | Glu | Leu | Leu | Ser | Gln | Leu | Gln | Glu | Gly | Glu | Phe | Trp | Val | |
| | | 290 | | | | | 295 | | | | | 300 | | | | |
| gag | gag | gag | gag | ttc | ctc | agg | gag | ttt | gac | gag | ctc | acc | gtt | ggc | tac | 1139 |
| Glu | Glu | Glu | Glu | Phe | Leu | Arg | Glu | Phe | Asp | Glu | Leu | Thr | Val | Gly | Tyr | |
| 305 | | | | | 310 | | | | | 315 | | | | | | |
| ccg | gtc | acg | gag | gcc | ggc | cac | ctg | cag | agc | ctc | tac | aca | gag | agg | ctg | 1187 |
| Pro | Val | Thr | Glu | Ala | Gly | His | Leu | Gln | Ser | Leu | Tyr | Thr | Glu | Arg | Leu | |
| 320 | | | | | 325 | | | | | 330 | | | | | 335 | |
| ctc | tgc | cat | acg | cgg | gcg | ctg | cct | ggg | gcc | tgg | gtc | aag | ggc | cag | tca | 1235 |
| Leu | Cys | His | Thr | Arg | Ala | Leu | Pro | Gly | Ala | Trp | Val | Lys | Gly | Gln | Ser | |
| | | | 340 | | | | | 345 | | | | | 350 | | | |
| gca | gga | ggc | tgc | cgg | aac | aac | agc | ggc | ttt | ccc | agc | aac | ccc | aaa | ttc | 1283 |
| Ala | Gly | Gly | Cys | Arg | Asn | Asn | Ser | Gly | Phe | Pro | Ser | Asn | Pro | Lys | Phe | |
| | | | 355 | | | | | 360 | | | | | 365 | | | |
| tgg | ctg | cgg | gtc | tca | gaa | ccg | agt | gag | gtg | tac | att | gcc | gtc | ctg | cag | 1331 |
| Trp | Leu | Arg | Val | Ser | Glu | Pro | Ser | Glu | Val | Tyr | Ile | Ala | Val | Leu | Gln | |
| | | 370 | | | | | 375 | | | | | 380 | | | | |
| aga | tcc | agg | ctg | cac | gcg | gcg | gac | tgg | gca | ggc | cgg | gcc | cgg | gca | ctg | 1379 |
| Arg | Ser | Arg | Leu | His | Ala | Ala | Asp | Trp | Ala | Gly | Arg | Ala | Arg | Ala | Leu | |
| | 385 | | | | | 390 | | | | | 395 | | | | | |
| gtg | ggt | gac | agt | cat | act | tcg | tgg | agc | cca | gcg | agc | atc | ccg | ggc | aag | 1427 |
| Val | Gly | Asp | Ser | His | Thr | Ser | Trp | Ser | Pro | Ala | Ser | Ile | Pro | Gly | Lys | |
| 400 | | | | | 405 | | | | | 410 | | | | | 415 | |
| cac | tac | cag | gct | gtg | ggt | ctg | cac | ctc | tgg | aag | gtc | cca | gag | ggt | gga | 1475 |
| His | Tyr | Gln | Ala | Val | Gly | Leu | His | Leu | Trp | Lys | Val | Pro | Glu | Gly | Gly | |
| | | | 420 | | | | | 425 | | | | | 430 | | | |
| agg | agc | cag | gac | gca | ccc | cca | ctg | ctg | ctg | cag | gag | ccg | ctg | ctg | agc | 1523 |
| Arg | Ser | Gln | Asp | Ala | Pro | Pro | Leu | Leu | Leu | Gln | Glu | Pro | Leu | Leu | Ser | |
| | | | 435 | | | | | 440 | | | | | 445 | | | |
| tgc | gtg | cca | cat | cgc | tac | gcc | cag | gag | gtg | agc | cgg | ctc | tgc | ctc | ctg | 1571 |
| Cys | Val | Pro | His | Arg | Tyr | Ala | Gln | Glu | Val | Ser | Arg | Leu | Cys | Leu | Leu | |
| | | 450 | | | | | 455 | | | | | 460 | | | | |
| cct | gcg | ggc | acc | tac | aag | gtt | gtg | ccc | tcc | acc | tac | ctg | ccg | gac | aca | 1619 |
| Pro | Ala | Gly | Thr | Tyr | Lys | Val | Val | Pro | Ser | Thr | Tyr | Leu | Pro | Asp | Thr | |
| | 465 | | | | | 470 | | | | | 475 | | | | | |
| gag | ggg | gcc | ttc | aca | gtg | acc | atc | gca | acc | agg | att | gac | agg | cca | tcc | 1667 |
| Glu | Gly | Ala | Phe | Thr | Val | Thr | Ile | Ala | Thr | Arg | Ile | Asp | Arg | Pro | Ser | |
| 480 | | | | | 485 | | | | | 490 | | | | | 495 | |

-continued

| | | | | | | | | | | | | |
|---|---|---|---|---|---|---|---|---|---|---|---|---|
| att | cac | agc | cag | gag | atg | ctg | ggc | cag | ttc | ctc | caa | gag | gtc | tcc | gtc | 1715 |
| Ile | His | Ser | Gln | Glu | Met | Leu | Gly | Gln | Phe | Leu | Gln | Glu | Val | Ser | Val | |
| | | | 500 | | | | 505 | | | | 510 | | | | | | atg gca gtg atg aaa acc taa c agggtggccc cctgtgccag ctcaggtgac 1767
Met Ala Val Met Lys Thr *
515 tggagcccga gggcctgaca ggttcccagc agctgggccg ccagccttg cactgtgggg 1827 gctggtcctg agtcttggcc tgcctcccag ccctgccagg gggctgcggc ctaggggtcc 1887 acgggaagcc tccgtcagga gagacgcagc cctgggggcc agctggtgct gcaaggaagg 1947 gtgggaagct tgctggcttc tgttgcgcca ctgagacggc agagacccca ggatcccaga 2007 gcttcccagg atccctccca gatcctctgc tgactccata tggaggcctc acacccagag 2067 ggtagggcag cagatcttct ttataactat ttattgttcg aatcactttt aggatgtaac 2127 tttataaata aacatgagcg ctgatgattt gcaaaaaaaa aaaaaaaaaa aaa 2180

<210> SEQ ID NO 2
<211> LENGTH: 517
<212> TYPE: PRT
<213> ORGANISM: Homo sapiens

<400> SEQUENCE: 2

Met Arg Ala Gly Arg Gly Ala Thr Pro Ala Arg Glu Leu Phe Arg Asp
1               5                   10                  15

Ala Ala Phe Pro Ala Ala Asp Ser Ser Leu Phe Cys Asp Leu Ser Thr
            20                  25                  30

Pro Leu Ala Gln Phe Arg Glu Asp Ile Thr Trp Arg Arg Pro Gln Glu
        35                  40                  45

Ile Cys Ala Thr Pro Arg Leu Phe Pro Asp Asp Pro Arg Glu Gly Gln
    50                  55                  60

Val Lys Gln Gly Leu Leu Gly Asp Cys Trp Phe Leu Cys Ala Cys Ala
65                  70                  75                  80

Ala Leu Gln Lys Ser Arg His Leu Leu Asp Gln Val Ile Pro Pro Gly
                85                  90                  95

Gln Pro Ser Trp Ala Asp Gln Glu Tyr Arg Gly Ser Phe Thr Cys Arg
            100                 105                 110

Ile Trp Gln Phe Gly Arg Trp Val Glu Val Thr Thr Asp Asp Arg Leu
        115                 120                 125

Pro Cys Leu Ala Gly Arg Leu Cys Phe Ser Arg Cys Gln Arg Glu Asp
    130                 135                 140

Val Phe Trp Leu Pro Leu Leu Glu Lys Val Tyr Ala Lys Val His Gly
145                 150                 155                 160

Ser Tyr Glu His Leu Trp Ala Gly Gln Val Ala Asp Ala Leu Val Asp
                165                 170                 175

Leu Thr Gly Gly Leu Ala Glu Arg Trp Asn Leu Lys Gly Val Ala Gly
            180                 185                 190

Ser Gly Gly Gln Gln Asp Arg Pro Gly Arg Trp Glu His Arg Thr Cys
        195                 200                 205

Arg Gln Leu Leu His Leu Lys Asp Gln Cys Leu Ile Ser Cys Cys Val
    210                 215                 220

Leu Ser Pro Arg Ala Gly Ala Arg Glu Leu Gly Glu Phe His Ala Phe
225                 230                 235                 240

Ile Val Ser Asp Leu Arg Glu Leu Gln Gly Gln Ala Gly Gln Cys Ile
                245                 250                 255

-continued

```
Leu Leu Leu Arg Ile Gln Asn Pro Trp Gly Arg Arg Cys Trp Gln Gly
            260                 265                 270
Leu Trp Arg Glu Gly Gly Glu Gly Trp Ser Gln Val Asp Ala Ala Val
            275                 280                 285
Ala Ser Glu Leu Leu Ser Gln Leu Gln Glu Gly Glu Phe Trp Val Glu
            290                 295                 300
Glu Glu Glu Phe Leu Arg Glu Phe Asp Glu Leu Thr Val Gly Tyr Pro
305                 310                 315                 320
Val Thr Glu Ala Gly His Leu Gln Ser Leu Tyr Thr Glu Arg Leu Leu
                    325                 330                 335
Cys His Thr Arg Ala Leu Pro Gly Ala Trp Val Lys Gly Gln Ser Ala
                340                 345                 350
Gly Gly Cys Arg Asn Asn Ser Gly Phe Pro Ser Asn Pro Lys Phe Trp
            355                 360                 365
Leu Arg Val Ser Glu Pro Ser Glu Val Tyr Ile Ala Val Leu Gln Arg
            370                 375                 380
Ser Arg Leu His Ala Ala Asp Trp Ala Gly Arg Ala Arg Ala Leu Val
385                 390                 395                 400
Gly Asp Ser His Thr Ser Trp Ser Pro Ala Ser Ile Pro Gly Lys His
                    405                 410                 415
Tyr Gln Ala Val Gly Leu His Leu Trp Lys Val Pro Glu Gly Gly Arg
                420                 425                 430
Ser Gln Asp Ala Pro Pro Leu Leu Leu Gln Glu Pro Leu Leu Ser Cys
            435                 440                 445
Val Pro His Arg Tyr Ala Gln Glu Val Ser Arg Leu Cys Leu Leu Pro
450                 455                 460
Ala Gly Thr Tyr Lys Val Val Pro Ser Thr Tyr Leu Pro Asp Thr Glu
465                 470                 475                 480
Gly Ala Phe Thr Val Thr Ile Ala Thr Arg Ile Asp Arg Pro Ser Ile
                    485                 490                 495
His Ser Gln Glu Met Leu Gly Gln Phe Leu Gln Glu Val Ser Val Met
                500                 505                 510
Ala Val Met Lys Thr
            515
```

<210> SEQ ID NO 3
<211> LENGTH: 1554
<212> TYPE: DNA
<213> ORGANISM: Homo sapiens

<400> SEQUENCE: 3

```
atgcgggcgg gccggggcgc gacgccggcg agggagctgt tccgggacgc cgccttcccc      60
gccgcggact cctcgctctt ctgcgacttg tctacgccgc tggcccagtt ccgcgaggac     120
atcacgtgga ggcggcccca ggagatttgt gccacacccc ggctgtttcc agatgaccca     180
cgggaagggc aggtgaagca ggggctgctg gggattgct  ggttcctgtg tgcctgcgcc     240
gcgctgcaga agagcaggca cctcctggac caggtcattc ctccgggaca gccgagctgg     300
gccgaccagg agtaccgggg ctccttcacc tgtcgcattt ggcagtttgg acgctgggtg     360
gaggtgacca cagatgaccg cctgccgtgc cttgcaggga gactctgttt ctcccgctgc     420
cagagggagg atgtgttctg gctcccctta ctggaaaagg tctacgccaa ggtccatggg     480
tcctacgagc acctgtgggc cgggcaggtg gcggatgccc tggtggacct gaccggcggc     540
ctggcagaaa gatggaacct gaagggcgta gcaggaagcg gaggccagca ggacaggcca     600
```

-continued

```
ggccgctggg agcacaggac ttgtcggcag ctgctccacc tgaaggacca gtgtctgatc      660
agctgctgcg tgctcagccc cagagcaggt gcccgggagc tgggggagtt ccatgccttc      720
attgtctcgg acctgcggga gctccagggt caggcgggcc agtgcatcct gctgctgcgg      780
atccagaacc cctggggccg gcggtgctgg caggggctct ggagagaggg gggtgaaggg      840
tggagccagg tagatgcagc ggtagcatct gagctcctgt cccagctcca ggaaggggag      900
ttctgggtgg aggaggagga gttcctcagg gagtttgacg agctcaccgt tggctacccg      960
gtcacggagg ccgccacct gcagagcctc tacacagaga ggctgctctg ccatacgcgg     1020
gcgctgcctg gggcctgggt caagggccag tcagcaggag gctgccggaa caacagcggc     1080
tttcccagca accccaaatt ctggctgcgg gtctcagaac cgagtgaggt gtacattgcc     1140
gtcctgcaga gatccaggct gcacgcggcg gactgggcag gccgggcccg ggcactggtg     1200
ggtgacagtc atacttcgtg gagcccagcg agcatcccgg gcaagcacta ccaggctgtg     1260
ggtctgcacc tctggaaggt cccagagggt ggaaggagcc aggacgcacc cccactgctg     1320
ctgcaggagc cgctgctgag ctgcgtgcca catcgctacg cccaggaggt gagccggctc     1380
tgcctcctgc ctgcgggcac ctacaaggtt gtgccctcca cctacctgcc ggacacagag     1440
ggggccttca cagtgaccat cgcaaccagg attgacaggc catccattca cagccaggag     1500
atgctgggcc agttcctcca agaggtctcc gtcatggcag tgatgaaaac ctaa            1554
```

<210> SEQ ID NO 4
<211> LENGTH: 343
<212> TYPE: PRT
<213> ORGANISM: Artificial Sequence
<220> FEATURE:
<223> OTHER INFORMATION: PFAM consensus sequence for calpain family cystein protease

<400> SEQUENCE: 4

```
Leu Phe Glu Asp Pro Ser Phe Pro Ala Ala Pro Lys Ser Leu Gly Tyr
 1               5                  10                  15

Lys Pro Leu Gly Pro Ala Ser Ser Lys Thr Arg Gly Ile Glu Trp Lys
            20                  25                  30

Arg Pro His Glu Ile Asn Glu Asn Pro Gln Ala Tyr Pro Pro Trp Phe
        35                  40                  45

Ile Val Gly Gly Ala Ser Arg Thr Asp Ile Cys Gln Gly Ala Leu Gly
    50                  55                  60

Asp Cys Trp Leu Leu Ala Ala Ile Ala Ser Leu Thr Leu Asn Glu Glu
65                  70                  75                  80

Leu Leu Lys Arg Val Val Pro His Asp Gln Ser Phe Gln Glu Asn Trp
                85                  90                  95

Arg Leu Tyr Arg Tyr Ala Gly Ile Phe His Phe Arg Phe Trp Gln
            100                 105                 110

Tyr Gly Lys Trp Val Asp Val Val Asp Asp Leu Leu Pro Thr Lys
        115                 120                 125

Asp Gly Lys Val Pro Ile Leu Leu Phe Val His Ser Ala Glu Arg Asn
    130                 135                 140

Glu Phe Trp Ser Ala Leu Leu Glu Lys Ala Tyr Ala Lys Leu Asn Gly
145                 150                 155                 160

Cys Tyr Glu Ala Leu Tyr Asn Ala Ile Leu Gln Ile Ser Gly Gly Ser
                165                 170                 175

Thr Thr Glu Ala Leu Glu Asp Leu Thr Gly Gly Val Cys Glu Ser Tyr
            180                 185                 190
```

```
Glu Leu Lys Lys Ala Pro Ser Pro Met Pro Ser Glu Thr Asp Leu Asn
        195                 200                 205

Leu Leu Asn Ile Ile Lys Lys Ala Leu Glu Arg Gly Ser Asn Ser Leu
        210                 215                 220

Arg Asp Ser Asp Leu Val Arg Phe Leu Leu Leu Gly Cys Ser Ile Asp
225                 230                 235                 240

Ile Thr Ser Pro Val Asp Met Glu Ala Lys Met Ala Lys Gly Leu Val
                245                 250                 255

Lys Gly His Ala Tyr Ser Val Thr Gly Val Lys Glu Val Asn Tyr Arg
                260                 265                 270

Gly Glu Lys Gln Lys Leu Ile Arg Leu Arg Asn Pro Trp Gly Asp Glu
                275                 280                 285

Val Glu Trp Thr Gly Asp Trp Ser Asp Ser Ser Pro Asp Trp Arg Glu
        290                 295                 300

Ile Asp Glu Asp Glu Lys Ala Arg Leu Gln Leu Lys Phe Glu Glu Asp
305                 310                 315                 320

Gly Glu Phe Trp Met Ser Phe Glu Asp Phe Leu Asn His Phe Ser Arg
                325                 330                 335

Leu Glu Ile Cys Asn Leu Thr
        340

<210> SEQ ID NO 5
<211> LENGTH: 300
<212> TYPE: PRT
<213> ORGANISM: Artificial Sequence
<220> FEATURE:
<223> OTHER INFORMATION: ProDom consensus sequence for calpain protease

<400> SEQUENCE: 5

Leu Phe Glu Asp Pro Ser Phe Pro Pro Asn Pro Lys Ser Leu Gly Tyr
1               5                   10                  15

Lys Glu Leu Gly Pro Asn Ser Ser Lys Thr Lys Gly Ile Glu Trp Lys
                20                  25                  30

Arg Pro Ser Glu Ile Cys Ser Asn Pro Asp Asp His Ser Met Pro Gln
            35                  40                  45

Phe Ile Val Gly Gly Ala Thr Arg Thr Asp Ile Cys Gln Gly Thr Ala
        50                  55                  60

Leu Gly Asp Cys Trp Leu Leu Ala Ala Leu Ala Ser Leu Thr Leu Asn
65                  70                  75                  80

Glu Glu Leu Leu His Arg Val Ile Pro Asp His Ser Phe Gln Trp
                    85                  90                  95

Asp Pro Arg Lys Glu Asn Tyr Ala Gly Ile Phe His Phe Arg Phe Trp
            100                 105                 110

Gln Tyr Gly Glu Trp Val Asp Val Val Ile Asp Asp Tyr Leu Pro Thr
        115                 120                 125

Lys Asn Gly Glu Asn Ser Leu Ile Phe Val His Ser Asn Glu Arg Asn
    130                 135                 140

Glu Phe Trp Ser Ala Leu Leu Glu Lys Ala Tyr Ala Lys Leu His Gly
145                 150                 155                 160

Ser Tyr Glu Ala Leu Ser Gly Gly Asn Thr Ser Glu Ala Phe Glu Asp
                165                 170                 175

Phe Thr Gly Gly Val Cys Glu Trp Tyr Asp Leu Gln Lys Ser Thr Lys
            180                 185                 190

Ser Met Pro Lys Glu Ala Pro Ser Asp Thr Asp Gln Leu Trp Glu Ile
        195                 200                 205
```

-continued

```
Leu Met Lys Ala Leu Glu Arg Gly Ser Leu Met Gly Cys Ser Ile Asp
    210                 215                 220

Thr Val Thr Ser Ala Ala Glu Glu Glu Ala Gln Thr Glu Gln Gly Leu
225                 230                 235                 240

Val Lys Gly His Ala Tyr Ser Val Thr Asp Val Lys Glu Val Asn Tyr
                245                 250                 255

Arg Gly Gln Gly His Arg Leu Ile Arg Leu Arg Asn Pro Trp Gly Glu
                260                 265                 270

Val Glu Trp Asn Gly Pro Trp Ser Asp Asn Ser Pro Glu Trp Asn Ser
            275                 280                 285

Val Asp Lys Asp Glu Lys Glu Asn Met Gly Ser Gln
            290                 295                 300

<210> SEQ ID NO 6
<211> LENGTH: 7
<212> TYPE: PRT
<213> ORGANISM: Artificial Sequence
<220> FEATURE:
<223> OTHER INFORMATION: Calpastatin consensus binding site
<221> NAME/KEY: VARIANT
<222> LOCATION: (1)...(7)
<223> OTHER INFORMATION: Xaa = Any Amino Acid

<400> SEQUENCE: 6

Thr Ile Pro Pro Xaa Tyr Arg
1               5
```

18036, A NOVEL CALPAIN-LIKE PROTEASE AND USES THEREOF

CROSS-REFERENCE TO RELATED APPLICATION

This application claims the benefit of U.S. Provisional Application Serial No. 60/185,333 filed Feb. 28, 2000, which is hereby incorporated herein in its entirety by reference.

FIELD OF THE INVENTION

The invention relates to novel calpain-like protease nucleic acid sequences and proteins. Also provided are vectors, host cells, and recombinant methods for making and using the novel molecules.

BACKGROUND OF THE INVENTION

Calpains refer to calcium-activated neutral proteinases, a superfamily of endopeptidases typically having cysteine-proteinase and calcium-binding characteristics. These proteinases cleave numerous substrate proteins in a limited manner, typically leading to modification of the function and/or activity rather than general degradation of the substrate.

Calpains are classified into two main groups, the typical or conventional calpains and the atypical calpains, based on their domain content and/or variation. The typical calpains are further subdivided into ubiquitous and tissue-specific calpains based on their predominate patterns of expression.

Two forms of ubiquitous calpains have been extensively characterized in vertebrates: the $\mu$-calpains (calpain I, CAPN1) and the m-calpains (calpain II, CAPN2), which are activated in vitro by micro- and millimolar calcium concentrations, respectively. An intermediate $\mu$/m calpain has been characterized in chicken.

The ubiquitous $\mu$- and m-calpains are heterodimers, each having a distinct, but homologous, large 80 kDa subunit (referred to as $\mu$CL or mCL, respectively) and an identical small 30 kDa subunit (referred to as 30K or Cs). The large subunit has four domains, designated I–IV from the N-terminus to the C-terminus. The function of domain I is unclear. Domain II is the cysteine protease domain responsible for calpain protease activity. Domain III is homologous to a calmodulin-binding protein and is speculated to interact with the calcium-binding domains of the large (domain IV) and small subunits (domain VI), when calcium is bound, thereby freeing the protease domain for activity (Goll et al. (1992) *BioEssays* 14:549–556). Domain IV of the large subunit is a calmodulin-like calcium-binding domain containing four EF-hand calcium-binding motifs. Although structurally similar to calmodulin, domain IV is more similar to sorcin, ALG-2, and grancalcin. Sorcin is involved in the multi-drug resistance of cultured cell lines and was recently reported to associate with the cardiac ryanodine receptor. Grancalcin possibly plays a role in granule-membrane fusion and degranulation. ALG-2 is thought to be involved in apoptosis and is induced by tumor promoters. See Meyers et al. (1995) *J. Biol. Chem.* 270:26411–26418; Meyers et al. (1985) *J. Cell Biol.* 100:588–597, Vito et al. (1996) *Science* 271:521–525; Teahan et al. (1992) *Biochem. J.* 286:549–554; Boyhan et al. (1992) *J. Biol. Chem.* 267:2928–2933.

The large subunit of calpains is the catalytic subunit. Three non-contiguous amino acid residues, Cys, His, and Asn, residing within domain II are part of the active site. A recombinant calpain consisting essentially of domains I, II, and III showed calcium-independent activity. Thus, it has been concluded that domain II, but not IV, is necessary and sufficient for protease activity. See Vilei et al. (1997) *J. Biol. Chem.* 272:25802–25808; and Suzuki et al. (1998) *FEBS Letters* 433(1, 2):1–4.

The small subunit of typical calpains contains two domains, which are designated V and VI from the N-terminus to the C-terminus. Domain V is an N-terminal glycine-clustering hydrophobic region. Domain VI, which is similar to domain IV of the large subunit, is also a calcium-binding domain containing six EF-hands, EF2–EF5 as in the large subunit, and EF1 and EF6. EF5 of domain VI does not bind calcium and is proposed to be involved in the heterodimeric binding of domains IV and VI during interaction between the large and small subunits.

Not all calpains contain a small subunit, which is identified as a regulator of calpain activity by acting as an inhibitor or pseudosubstrate. In heterodimeric calpains, the small subunit may regulate the calcium-sensitivity of calpain by association and dissociation (Yoshizawa et al. (1995) *Biochem. Biophys. Res. Commun.* 208:376–383). However, the subunits remain associated during catalysis (Zhang et at. (1996) *Biochem. Biophys. Res. Commun.* 227:890–896).

The mechanism of activation of calpains is not entirely clear. Suggested mechanisms include combinations of N-terminal autolysis of subunits, homo- and heterodimer association/dissociation, the ratio and binding status of calpains to the calpain endogenous inhibitor calpastatin, calcium presence and concentration, and the redox state of the active site. See Johnson et al. (1997) *BioEssays* 19(11):1011–1018.

Because $\mu$- and m-calpain are activated by in vitro calcium concentrations significantly above physiological levels, in vivo mechanisms that lower the calcium requirement have been proposed. Such mechanisms include interactions with membrane phospholipids and/or membrane associated proteins. See Inomata et al. (1990) *Biochem. Biophys. Res. Comm.* 171:625–632; and Inomata et al. (1995) *Biochim. Biophys. Acta.* 1235:107–114.

An activator protein specific for rat brain $\mu$-calpain has been isolated and sequenced by Melloni et al. (1998) *J. Biol. Chem.* 273:12827–12831. Another activator protein specific for m-calpain is found in skeletal muscle. In addition, phospholipids, especially acidic phospholipids, have been found to greatly reduce the calcium concentration necessary for activation. Other activators and factors including DNA have been reported (Mellgren (1991) *J. Biol. Chem.* 266:13920–13924).

Calpastatin is an endogenous inhibitor of most calpains, the tissue-specific calpain p94 being an exception. Calpastatin, which has five domains, is cleaved by calpain in the interdomain regions, generating inhibitory peptides. The inhibitory effect of calpastatin has been attributed to interactions with calpain domains II, III, IV, and VI. The reactive site of calpastatin shows no apparent homology to that of other protease inhibitors, and it contains the consensus sequence TIPPXYR (SEQ ID NO:6), which is essential for inhibition. See Kawasaki et al. (1989) *J. Biochem.* 106:274–281, Croall et al. (1994) *Biochem.* 33:13223–13230; Croall et al. (1991) *Physiol. Rev.* 71:813–847; Kawasaki et al. (1996) *Mol. Membr. Biol.* 13:217–224; Melloni et al. (1989) *Trends Neurosci.* 12:438–444; Sorimachi et al. (1997) *J. Biochem.* 328:721–732; and Johnson et al. (1997) *BioEssays* 19(11):1011–1018.

Synthetic active-site inhibitors with varying specificities for calpain and other cysteine proteases include E-64 and derivatives of E-64; leupeptin (N-acetyl-Leu-Leu-argininal); calpain inhibitors I (N-acetyl-Leu-Leu-norleucinal) and II (N-acetyl-Leu-Leu-methioninal); oxoamide inhibitor molecules AK295, AK275, and CX275; and derivatives of peptidyl α-oxo compounds. In contrast to these active-site inhibitors, PD150606 inhibits calpains by binding the calcium-binding domains. The combination of PD150606 and an active site inhibitor such as AK295 can inhibit calpain with high specificity. See Figueiredo-Pereira et al. (1994) *J. Neuro. Chem.* 62:1989–1994); Tsubuki et al. (1996) *J. Biochem. (Tokyo)* 119:572–576); and Sorimachi et al. (1997) *J. Biochem.* 328:721–732. Wang et al (1997) *Advances in Pharmacology,* Volume 37.

Several typical tissue-specific calpains are known in vertebrates, including skeletal muscle p94 (nCL-1, calpain 3', CAPN3), stomach nCL2 (CAPN4) and nCL 2', and digestive tubule nCL4. While p94 contains EF hands, it does not require calcium for proteinase activity. p94 has a domain IV sequence similar to that of μCL and mCL, but it does not bind to a small 30 kDa subunit (Kinbara et al. (1997) *Arch. Biochem. Biophys.* 342:99–107). p94 contains unique insertion sequences called IS1 and IS2, which are found in domain II and between domains III and IV, respectively). IS2 contains a nuclear-localization-signal-like basic sequence (Arg-Pro-Xaa-Lys-Lys-Lys-Lys-x-Lys-Pro). Connectin/titin binding is also attributed to IS2. p94 may change its localization in a cell-cycle dependent manner and may be involved in muscle differentiation by interacting with the MyoD family. In fact, a defect in the protease p94 is responsible for limb-girdle muscular dystrophy type 2A (LGMD2A). See Sorimachi et al. (1995) *J. Biol. Chem.* 270:31158–31162; Sorimachi et al. (1993) *J. Biol. Chem.* 268:10593–10605; Gregoriou et al. (1994) *Eur. J. Biochem.* 223:455–464; and Belcastro et al. (1998) *Mol. Cell. Biochem.* 179 (1, 2):135–145.

Atypical calpains include the fungal protein PalB, the yeast PalB homolog, the *Caenorhabditis elegans* protein Tra-3, human CAPN5 (htra3), CAPN6, and murine CAPN7. Although atypical calpains have a cysteine protease domain homologous to domain II of the large subunit of typical calpains, they lack a calcium-binding domain in the C-terminal portion of the protein (domain IV). See Suzuki et al. (1998) *FEBS Letters* 433(1, 2):1–4; Sorimachi et al. (1997) *J. Biochem.* 328:721–732; Franz et al. (1999) *Mammalian Genome* 10(3):318–321; Goll et al. (1992) *BioEssays* 14:549–556; and Lin et al. (1997) *Nature Struct. Biol.* 4:539–547.

PalB, which is involved in the alkaline adaptation of *Aspergillus nidulans*, is unusual in that it only has a cysteine protease domain. Tra3, which is involved in the sex-determination cascade during early development, has domains similar to domains I, II, and III of the typical calpain large subunit. Human and mouse Tra3 homologs have been identified and localized to x chromosomes, suggesting a role for calpain in sex determination in mammals. See Barnes et al. (1996) *EMBO J.* 15:44774484; and Sorimachi et al. (1997) *J. Biochem.* 328:721–732.

The atypical mammalian calpains include CAPN5, 6, and 7. CAPN6 and 7 contain distinct T domains in their C-terminal regions and may not associate with small subunits. These T domains have no significant homology to the calmodulin-like calcium-binding C-terminal domain of other calpains. Furthermore, CAPN6 lacks residues believed to be critical for the active site and may lack protease activity. See Franz et al. (1999) *Mammalian Genome* 10(3):318–321.

Calpains have broad physiological and pathological roles related to the enzymes' diverse population of substrates. Calpain substrates include "PEST" proteins, which have high proline, glutamine, serine, and threonine contents; calpain and calpastatin; signal transduction proteins including protein kinase C, transcription factors c-Jun, c-Fos, and α-subunit of heterotrimeric G proteins; proteins involved in cell proliferation and cancer including P53 tumor suppressor, growth factor receptors (e.g., epidermal growth factor receptor), c-Jun, c-Fos, and N-myc; proteins with established physiological roles in muscle including $Ca^{++}$-ATPase, Band III, troponin, tropomyosin, and myosin light chain kinase; myotonin protein kinase; proteins with established physiological roles in the brain and the central nervous system including myelin proteins, myelin basic protein (MBP), axonal neurofilament protein (NFP), myelin protein MAG; cytosketetal and cell adhesion proteins including troponins, talin, neurofilaments, spectrin, microtubule associated protein MAP-2, tau, MAPIB, fodrin, desmin, α-actinin, vimentin, spectrin, integrin, cadherin, filamin, and N-CAM; enzymes including protein kinases A and C, and phospholipase C; and histones. See Sorimachi et al. (1997) *J. Biochem.* 328:721–732; Johnson et al. (1997) *BioEssays* 19(11): 1011–1018; Shields et al. (1999) *J. Neuroscience Res.* 55(5):533–541; and Belcastro et al. (1998) *Mol. Cell. Biochem.* 179 (1, 2): 135–145.

Substrates of calpain have been associated into several classes including cytoskeletal and structural proteins, membrane bound receptors and proteins, calmodulin binding proteins, enzymes myofibrillar proteins and transcription factors. The examples of the first group include spectrin, MAP-2a, tau factor, neurofilament H, M and L, α-actinin. Examples of the second class include EGF receptor, AMPA-receptor, calcium pump, anion channel, calcium release channel, L-type calcium channel, G-proteins. Examples of the third class include calcium pump, calcineurin, CaM-dependent protein kinase II, myosin light chain kinase, neuromodulin, connexins, IP3 kinase. Examples of the fourth group include protein kinase C, HMG-CoA reductase, cAMP-dependent kinase, pyruvate kinase, phosphorylase kinase. Examples of the fifth group include troponin I, troponin T, tropomyosin, myosin.. Examples of the sixth group include c-fos, c-jun, Pit-1, Oct-1, and b, c-Myc. See Wang, et al. (1997) *Advances in Pharmacology*, Volume 37).

Calpain is implicated in a wide variety of physiological processes including alteration of membrane morphology, long-term potentiation of memory, axonal regeneration, neurite extension, cell proliferation (division), gastric HCl secretion, embryonic development, secretory granule movement, cell differentiation and regulation, cytoskeletal and membrane changes during cell migration, cytoskeletal remodeling, sex determination, and alkaline adaptation in fungi. See Solary et al. (1998) *Cell Biol. Toxicol.* 14:121–132; Sorimachi et al. (1997) *J. Biochem.* 328:721–732, Johnson et al. (1997) *BioEssays* 19(11):1011–1018; Suzuki et al. (1998) *FEBS Letters* 433(1, 2):1–4, Franz et al. (1999) *Mammalian Genome* 10(3):318–321; Shields et al. (1999) *J. Neuroscience Res.* 55(5):533–541, Schnellmann et al. (1998) *Renal Failure* 20(5):679–686; Banik et al. (1998) *Annals New York Acad. Sci.* 844:131–137; Belcastro et al. (1998) *Mol. Cell. Biochem.* 179 (1, 2):135–145; and McIntosh et al. (1998) *J. Neurotrauma* 15(10):731–769.

Under pathological conditions, aberrant regulation and/or activity of calpain can be detrimental to cells and tissues. In this context, calpains are implicated in a wide variety of disease states including exercise-induced injury and repair;

apoptosis including T cell receptor-induced apoptosis, HIV-infected cell apoptosis, ectoposide-treated cell apoptosis, nerve growth factor deprived neuronal apoptosis; ischemia, such as cerebral and myocardial ischemia, traumatic brain injury; Alzheimer's disease and other neurodegenerative diseases; demyelinating diseases including experimental allergic encephalomyelitis (EAE) and multiple sclerosis; LGMD2A muscular dystrophy; spinal cord injury (SCI); cancer; cataract formation; and renal cell death by diverse toxicants.

Optic nerve degeneration is one of the most common features of optic neuritis that leads to impaired vision and possible blindness. This condition is one of the first manifestations of multiple sclerosis. The mechanism of optic nerve degeneration in optic neuritis has been studied in experimental allergic encephalomyelitis, an animal model of optic neuritis. Calpain is present in the central nervous system and degrades myelin proteins. The role of calpain in demyelination associated with optic neuritis has been evaluated in rats with experimental optic neuritis. The results show that increased activity and translational expression of calpain in optic neuritis may be integral to the pathogenesis of this disorder. See Banik et al. (1999) *Histol Histopathol* 14: 649–656. The pathophysiological role of calpain in experimental demyelination has also been reviewed in Shields et al. (1999) *Journal of Neuroscience Research* 55:533–541.

Abnormality of protease activities and the imbalance of intracellular calcium are two key defects in Alzheimer's disease. Accordingly, it has been suggested that calcium dependent proteases such as calpain, as a critical link between these two events, must play a key role in the pathogenesis of Alzheimer's disease, and especially in abnormal processing of beta-amyloid precursor protein. See Chen, et al., (1998) *Frontiers in Bioscience* 3, a66–75. Further, calpains have been implicated in renal cell death. Schnellmann et al. ((1998) *Renal Failure*, 20(5): 679–686) showed that the inhibition of calpain activity decreased cell death produced by various toxicants. The role of calpain has also been studied in exercise-induced muscle injury. See Belcastro et al. (1998) *Molecular and Cellular Biochemistry* 179:135–145. The role of calpain homologs has been reviewed by Sorimachi et al. (1997) *Biochem, J.* 328:721–732. For example, one mammalian homolog, predominantly expressed in skeletal muscle has shown to be responsible for limb girdle muscular dystrophy type 2a. Another calpain homolog in nematodes is involved in the sex determination cascade during early development. Such calpain homologs in mammals have been found to be predominantly expressed in a limited number of organs in contrast with the ubiquitous expression of the more common calpains. These tissue-specific calpains include skeletal muscle-specific and stomach-specific. These homologs contain a cysteine-protease domain showing similarity to the more common calpain large subunit than to other cysteine proteases. However, they are atypical in that their other domains do not necessarily resemble conventional calpain large subunits. These have been reviewed in Sorimachi et al., above. Calcium isoforms in subunits are shown in, for example, Wang et al.(1997) *Advances in Pharmacology* 37:117–152.

Evidence has also suggested that calpains play a role in the pathology of cerebral ischemia. See Zalewska (1996) *Folia Neuropathol.* 34.3. Suppressive and protective effects of calpain inhibitors has been shown on post-ischemic damage. This subject has been reviewed in Zalewska. Silver et al. (1996) *Clinical Neuropharmacology* 19:101–128 has reviewed various medical therapies for ischemic stroke. This includes cytoprotective therapy with drugs that prevent ischemia and reperfusion including calpain inhibitors.

Given the diversity of calpains in cellular processes and disease states, compositions and methods directed to calpains are useful to influence calpain activity in a variety of tissues, thereby extending protection to cells and tissues affected with aberrant calpain function and/or regulation.

SUMMARY OF THE INVENTION

Isolated nucleic acid molecules corresponding to calpain-like protease nucleic acid sequences are provided. Additionally, amino acid sequences corresponding to the polynucleotides are encompassed. In particular, the present invention provides for isolated nucleic acid molecules comprising nucleotide sequences encoding the amino acid sequence shown in SEQ ID NO:2 or the nucleotide sequences encoding the DNA sequence deposited in a bacterial host with the ATCC as Patent Deposit Number PTA-2203. Further provided are calpain-like protease polypeptides having an amino acid sequence encoded by a nucleic acid molecule described herein.

The present invention also provides vectors and host cells for recombinant expression of the nucleic acid molecules described herein, as well as methods of making such vectors and host cells and for using them for production of the polypeptides or peptides of the invention by recombinant techniques.

Another aspect of this invention features isolated or recombinant calpain-like protease proteins and polypeptides. Preferred calpain-like protease proteins and polypeptides possess at least one biological activity possessed by naturally occurring calpain-like protease proteins.

Variant nucleic acid molecules and polypeptides substantially homologous to the nucleotide and amino acid sequences set forth in the sequence listing are encompassed by the present invention. Additionally, fragments and substantially homologous fragments of the nucleotide and amino acid sequences are provided.

Antibodies and antibody fragments that selectively bind the calpain-like protease polypeptides and fragments are provided. Such antibodies are useful in detecting the calpain-like protease polypeptides as well as in regulating the T-cell immune response and cellular activity, particularly growth and proliferation.

In another aspect, the present invention provides a method for detecting the presence of calpain-like protease activity or expression in a biological sample by contacting the biological sample with an agent capable of detecting an indicator of calpain-like protease activity such that the presence of calpain-like protease activity is detected in the biological sample.

In yet another aspect, the invention provides a method for modulating calpain-like protease activity comprising contacting a cell with an agent that modulates (inhibits or stimulates) calpain-like protease activity or expression such that calpain-like protease activity or expression in the cell is modulated. In one embodiment, the agent is an antibody that specifically binds to calpain-like protease protein. In another embodiment, the agent modulates expression of calpain-like protease protein by modulating transcription of a calpain-like protease gene, splicing of a calpain-like protease mRNA, or translation of a calpain-like protease mRNA. In yet another embodiment, the agent is a nucleic acid molecule having a nucleotide sequence that is antisense to the coding strand of the calpain-like protease mRNA or the calpain-like protease gene.

In one embodiment, the methods of the present invention are used to treat a subject having a disorder characterized by aberrant calpain-like protease protein activity or nucleic acid expression by administering an agent that is a calpain-like protease modulator to the subject. In one embodiment, the calpain-like protease modulator is a calpain-like protease protein. In another embodiment, the calpain-like protease modulator is a calpain-like protease nucleic acid molecule. In other embodiments, the calpain-like protease modulator is a peptide, peptidomimetic, or other small molecule.

The present invention also provides a diagnostic assay for identifying the presence or absence of a genetic lesion or mutation characterized by at least one of the following: (1) aberrant modification or mutation of a gene encoding a calpain-like protease protein; (2) misregulation of a gene encoding a calpain-like protease protein; and (3) aberrant post-translational modification of a calpain-like protease protein, wherein a wild-type form of the gene encodes a protein with a calpain-like protease activity.

In another aspect, the invention provides a method for identifying a compound that binds to or modulates the activity of a calpain-like protease protein. In general, such methods entail measuring a biological activity of a calpain-like protease protein in the presence and absence of a test compound and identifying those compounds that alter the activity of the calpain-like protease protein.

The invention also features methods for identifying a compound that modulates the expression of calpain-like protease genes by measuring the expression of the calpain-like protease sequences in the presence and absence of the compound.

Other features and advantages of the invention will be apparent from the following detailed description and claims.

BRIEF DESCRIPTION OF THE DRAWINGS

FIG. 1 shows the 18036 calpain-like protease nucleotide sequence (SEQ ID NO:1) and the deduced amino acid sequence (SEQ ID NO:2). The 18036 coding sequence in shown in SEQ ID NO:3.

FIG. 3 shows a 18036 calpain-like protease (SEQ ID NO:2) hydrophobicity plot. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:2) of human 18036 are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or an N-glycosylation site.

FIG. 4 shows an analysis of the 18036 calpain-like protease open reading frame (SEQ ID NO:2) indicating the locations of predicted functional sites.

FIG. 5 shows PSORT prediction of protein localization for the 18036 calpain-like protease.

FIG. 6 shows relative expression of 18036 in various human tissue samples.

FIG. 7 shows the alignment of the calpain cysteine protease domain of human 18036 with a consensus amino acid sequence derived from a hidden Markov model (PFAM Accession No. PF00648). The upper sequence is the consensus amino acid sequence (SEQ ID NO:4), while the lower amino acid sequence corresponds to amino acids 13 to 322 of SEQ ID NO:2.

FIG. 8 shows the alignment of the calpain cysteine protease domain of human 18036 with a ProDom consensus sequence (ProDom Accession No. PD002154). The lower sequence is the consensus amino acid sequence (SEQ ID NO:5), while the upper amino acid sequence corresponds to amino acids 13 to 295 of SEQ ID NO:2.

DETAILED DESCRIPTION OF THE INVENTION

Figure 2:
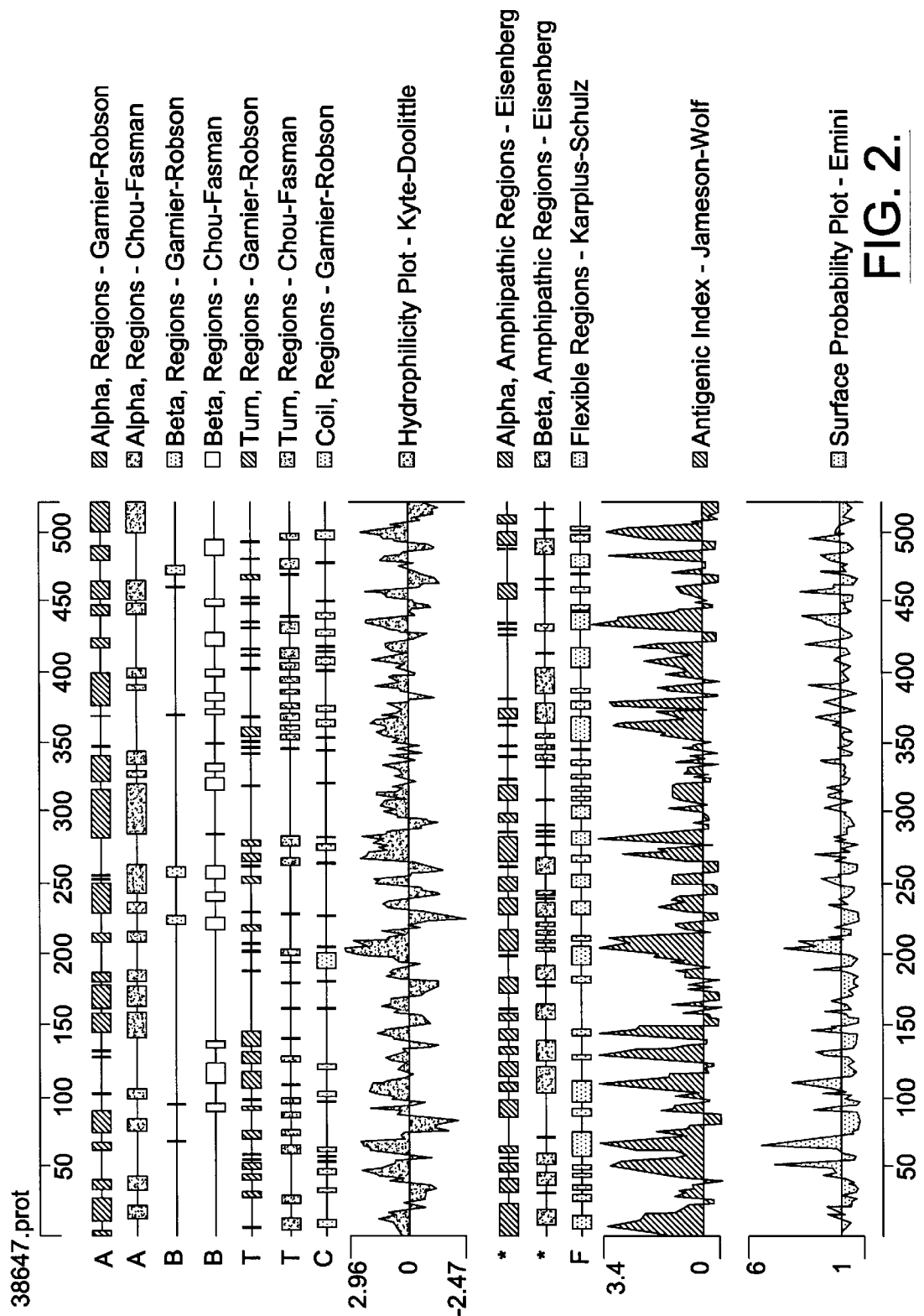
FIG. 2 shows an analysis of the 18036 calpain-like protease amino acid sequence: αβturn and coil regions; hydrophilicity; amphipathic regions; flexible regions; antigenic index; and surface probability plot. These regions are useful with respect to, among other things, generating antigenic fragments.

The present invention provides isolated nucleic acid molecules comprising nucleotide sequences encoding the calpain-like protease polypeptide whose amino acid sequence is given in SEQ ID NO:2, or a variant or fragment of the polypeptide. Nucleotide sequences encoding the calpain-like protease polypeptides of the invention are set forth in SEQ ID NO:1 and SEQ ID NO:3. The sequences are members of the calpain-like family of thiol proteases, also referred to as the peptidase family C2.

Calpain proteases are endopeptidases whose cleavage sites are typically between, rather than within, functional domains. As a result, enzyme substrates of calpain-like proteases are often activated rather than degraded, and other proteins are generally altered in their function rather than destroyed. Calpain proteases are generally calcium-dependent, and are thought to mediate intracellular calcium signaling. Controlled activation of these proteases apparently is central to a number of physiological processes, including, but not limited to, cyto/karyoskeletal remodeling, platelet activation, and cellular division, proliferation, development, and differentiation.

The disclosed invention relates to methods and compositions for the modulation, diagnosis, and treatment of calpain-like protease-mediated disorders. Such disorders include, but are not limited to, disorders associated with perturbed cellular growth and differentiation; exercise-induced injury and repair; apoptosis including T-cell receptor-induced apoptosis, HIV-infected cell apoptosis, ectoposide-treated cell apoptosis, nerve growth factor deprived neuronal apoptosis; ischemia; traumatic brain injury; Alzheimer's disease and other neurodegenerative diseases; demyelinating diseases including experimental allergic encephalomyelitis (EAE) and multiple sclerosis; LGMD2A muscular dystrophy; spinal cord injury (SCI); proliferative disorders or differentiative disorders such as cancer, e.g., melanoma, prostate cancer, cervical cancer, breast cancer, colon cancer, or sarcoma; and renal cell death associated with diverse toxicants.

The sequences of the invention find use in diagnosis of disorders involving an increase or decrease in protease expression relative to normal expression, such as a proliferative disorder, a differentiative disorder, or a developmental disorder. The sequences also find use in modulating protease-related responses. By "modulating" is intended the upregulating or downregulating of a response. That is, the compositions of the invention affect the targeted activity in either a positive or negative fashion.

One embodiment of the invention features protease nucleic acid molecules, preferably human protease molecules, which were identified based on a consensus motif or protein domain characteristic of the calpain-like family of thiol proteases. Specifically, a novel human gene, termed clone h18036, is provided. This sequence, and other nucleotide sequences encoding the h18036 protein or fragments and variants thereof, are referred to as "calpain-like protease sequences" indicating that the sequences share sequence similarity to other calpain-like protease genes.

Chromosome mapping analysis with WI-15718 has localized the gene to chromosome 2 between D2S140 and D2S2338 (272.5–277cM).

A plasmid containing the h18036 cDNA insert was deposited with the Patent Depository of the American Type Culture Collection (ATCC), 10801 University Boulevard, Manassas, Va., 20110-2209 on Jul. 7, 2000, and assigned Patent Deposit Number PTA-2203. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The calpain-like protease sequences of the invention are members of a protease family of molecules having conserved functional features. The term "family" when referring to the proteins and nucleic acid molecules of the invention is intended to mean two or more proteins or nucleic acid molecules having sufficient amino acid or nucleotide sequence identity as defined herein. Such family members can be naturally occurring and can be from either the same or different species. For example, a family can contain a first protein of murine origin and an ortholog of that protein of human origin, as well as a second, distinct protein of human origin and a murine ortholog of that protein. Members of a family may also have common functional characteristics.

Preferred calpain-like protease polypeptides of the present invention have an amino acid sequence sufficiently identical to the amino acid sequence of SEQ ID NO:2. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 60%, 65%, 70%, 75%, 80%, 85%, or 90% identity, preferably 91%, 92%, 93%, 94%, 95%, 96%, 97%, 98%, 99%, or more identity are defined herein as sufficiently identical.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (1970) J. Mol. Biol. 48:444–453 algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (1989) CABIOS 4:11–17 which has been incorporated into the ALIGN program (version 2.0), using a PAM 120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al (1990) J. Mol. Biol. 215:403–10. BLAST nucleotide searches can be performed with the NBLAST program, score=100, wordlength=12 to obtain nucleotide sequences homologous to 18036 nucleic acid molecules of the invention BLAST protein searches can be performed with the XBLAST program, score=50, wordlength=3 to obtain amino acid sequences homologous to 18036 protein molecules of the invention. To obtain gapped alignments for comparison purposes, Gapped BLAST can be utilized as described in Altschul et al. (1997) Nucleic Acids Res. 25(17):3389–3402. When utilizing BLAST and Gapped BLAST programs, the default parameters of the respective programs (e.g., XBLAST and NBLAST) can be used.

Accordingly, another embodiment of the invention features isolated calpain-like protease proteins and polypeptides having a calpain-like protease protein activity. As used interchangeably herein, a "calpain-like protease protein activity", "biological activity of a calpain-like protease protein", or "functional activity of a calpain-like protease protein" refers to an activity exerted by a calpain-like protease protein, polypeptide, or nucleic acid molecule on a calpain-like-protease-responsive cell as determined in vivo, or in vitro, according to standard assay techniques. A calpain-like protease activity can be a direct activity, such as an association with or an enzymatic activity on a second protein, or an indirect activity, such as a cellular signaling activity mediated by interaction of the calpain-like protease protein with a second protein. In a preferred embodiment, a calpain-like protease activity includes at least one or more of the following activities: (1) modulating (stimulating and/or enhancing or inhibiting) cellular proliferation, differentiation, and/or function (e.g., in cells in which it is expressed, for example, as shown in FIG. 6, such as thyroid, spleen, brain, and aorta); (2) modulating a calpain-like protease response; (3) modulating the entry of cells into mitosis; (4) modulating cellular differentiation; and (5) modulating cell death.

An "isolated" or "purified" calpain-like protease nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated calpain-like protease nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A calpain-like protease protein that is substantially free of cellular material includes preparations of calpain-like protease protein having less than about 30%, 20%, 10%, or 5% (by dry weight) of non-calpain-like protease protein (also referred to herein as a "contaminating protein"). When the calpain-like protease protein or biologically active portion thereof is recombinantly produced, preferably, culture medium represents less than about 30%, 20%, 10%, or 5% of the volume of the protein preparation. When calpain-like protease protein is produced by chemical synthesis, preferably the protein preparations have less than about 30%, 20%, 10%, or 5% (by dry weight) of chemical precursors or non-calpain-like protease chemicals.

Various aspects of the invention are described in further detail in the following subsections.

I. Isolated Nucleic Acid Molecules

One aspect of the invention pertains to isolated nucleic acid molecules comprising nucleotide sequences encoding calpain-like protease proteins and polypeptides or biologically active portions thereof, as well as nucleic acid molecules sufficient for use as hybridization probes to identify calpain-like protease -encoding nucleic acids (e.g., calpain-like protease mRNA) and fragments for use as PCR primers for the amplification or mutation of calpain-like protease nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the calpain-like protease proteins of the present invention include sequences set forth in SEQ ID NO:1, SEQ ID NO:3, the nucleotide sequence of the cDNA insert of the plasmid deposited with the ATCC as Patent Deposit Number PTA-2203 (the "cDNA of Patent Deposit Number PTA-2203"), and complements thereof. By "complement" is intended a nucleotide sequence that is sufficiently complementary to a given nucleotide sequence such that it can hybridize to the given nucleotide sequence to thereby form a stable duplex. The corresponding amino acid sequence for the calpain-like protease protein encoded by these nucleotide sequences is set forth in SEQ ID NO:2.

Nucleic acid molecules that are fragments of these calpain-like protease nucleotide sequences are also encompassed by the present invention. By "fragment" is intended a portion of the nucleotide sequence encoding a calpain-like protease protein. A fragment of a calpain-like protease nucleotide sequence may encode a biologically active portion of a calpain-like protease protein, or it may be a fragment that can be used as a hybridization probe or PCR primer using methods disclosed below. A biologically active portion of a calpain-like protease protein can be prepared by isolating a portion of one of the calpain-like protease nucleotide sequences of the invention, expressing the encoded portion of the calpain-like protease protein (e.g., by recombinant expression in vitro), and assessing the activity of the encoded portion of the calpain-like protease protein. Nucleic acid molecules that are fragments of a calpain-like protease nucleotide sequence comprise at least about 10, 15, 20, 25, 30, 35, 40, 45, 50, 65, 70, 75, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, or 2100 nucleotides, or up to the number of nucleotides present in a full-length calpain-like protease nucleotide sequence disclosed herein depending upon the intended use.

Alternatively, a nucleic acid molecule that is a fragment of an 18036-like nucleotide sequence of the present invention comprises a nucleotide sequence consisting of nucleotides 1–100, 101–200, 201–300, 301–400, 401–500, 501–600, 601–700, 701–800, 801–900, 901–1000, 1101–1200, 1201–1300, 1301–1400, 1401–1500, 1501–1600, 1601–1700, 1701–1800, 1801–1900, 1901–2000, 2001–2100, or 2101–2180 of SEQ ID NO:1.

It is understood that isolated fragments include any contiguous sequence not disclosed prior to the invention as well as sequences that are substantially the same and which are not disclosed. Accordingly, if an isolated fragment is disclosed prior to the present invention, that fragment is not intended to be encompassed by the invention. When a sequence is not disclosed prior to the present invention, an isolated nucleic acid fragment is at least about 10, 15, 20, 25, or 30 contiguous nucleotides. Other regions of the nucleotide sequence may comprise fragments of various sizes, depending upon potential homology with previously disclosed sequences.

A fragment of a calpain-like protease nucleotide sequence that encodes a biologically active portion of a calpain-like protease protein of the invention will encode at least 15, 25, 30, 50, 75, 100, 125, 150, 175, 200, 250, 300, 350, 400, 450, 500, contiguous amino acids, or up to the total number of amino acids present in a full-length calpain-like protease protein of the invention (for example, 517 amino acids for SEQ ID NO:2). Fragments of a calpain-like protease nucleotide sequence that are useful as hybridization probes for PCR primers generally need not encode a biologically active portion of a calpain-like protease protein.

Nucleic acid molecules that are variants of the calpain-like protease nucleotide sequences disclosed herein are also encompassed by the present invention. "Variants" of the calpain-like protease nucleotide sequences include those sequences that encode the calpain-like protease proteins disclosed herein but that differ conservatively because of the degeneracy of the genetic code. These naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the calpain-like protease proteins disclosed in the present invention as discussed below. Generally, nucleotide sequence variants of the invention will have at least 45%, 55%, 65%, 75%, 85%, 90%, 91%, 92%, 93%, 94%, 95%, 96%, 97%, 98%, or 99% identity to a particular nucleotide sequence disclosed herein. A variant calpain-like protease nucleotide sequence will encode a calpain-like protease protein that has an amino acid sequence having at least 45%, 55%, 65%, 75%, 85%, 90%, 91%, 92%, 93%, 94%, 95%, 96%, 97%, 98%, or 99% identity to the amino acid sequence of a calpain-like protease protein disclosed herein.

In addition to the calpain-like protease nucleotide sequences shown in SEQ ID NO:1 and SEQ ID NO:3, and the nucleotide sequence of the cDNA of Patent Deposit Number PTA-2203, it will be appreciated by those skilled in the art that DNA sequence polymorphisms that lead to changes in the amino acid sequences of calpain-like protease proteins may exist within a population (e.g., the human population). Such genetic polymorphism in a calpain-like protease gene may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding a calpain-like protease protein, preferably a mammalian calpain-like protease protein. As used herein, the phrase "allelic variant" refers to a nucleotide sequence that occurs at a calpain-like protease locus or to a polypeptide encoded by the nucleotide sequence. Such natural allelic variations can typically result in 1–5% variance in the nucleotide sequence of the calpain-like protease gene. Any and all such nucleotide variations and resulting amino acid polymorphisms or variations in a calpain-like protease sequence that are the result of natural allelic variation and that do not alter the functional activity of calpain-like protease proteins are intended to be within the scope of the invention.

Moreover, nucleic acid molecules encoding calpain-like protease proteins from other species (calpain-like protease homologs), which have a nucleotide sequence differing from that of the calpain-like protease sequences disclosed herein, are intended to be within the scope of the invention. For example, nucleic acid molecules corresponding to natural allelic variants and homologs of the human calpain-like protease cDNA of the invention can be isolated based on their identity to the human calpain-like protease nucleic acid disclosed herein using the human cDNA, or a portion thereof, as a hybridization probe according to standard hybridization techniques under stringent hybridization conditions as disclosed below.

In addition to naturally-occurring allelic variants of the calpain-like protease sequences that may exist in the population, the skilled artisan will further appreciate that changes can be introduced by mutation into the nucleotide sequences of the invention thereby leading to changes in the amino acid sequence of the encoded calpain-like protease proteins, without altering the biological activity of the calpain-like protease proteins. Thus, an isolated nucleic acid molecule encoding a calpain-like protease protein having a sequence that differs from that of SEQ ID NO:2 can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of a calpain-like protease protein (e.g., the sequence of SEQ ID NO:2) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif, such as the calpain-like family cysteine protease domain or calpain-like large subunit domain III, where such residues are essential for protein activity.

Alternatively, variant calpain-like protease nucleotide sequences can be made by introducing mutations randomly along all or part of a calpain-like protease coding sequence, such as by saturation mutagenesis, and the resultant mutants can be screened for calpain-like protease biological activity to identify mutants that retain activity. Following mutagenesis, the encoded protein can be expressed recombinantly, and the activity of the protein can be determined using standard assay techniques.

Thus the nucleotide sequences of the invention include the sequences disclosed herein as well as fragments and variants thereof. The calpain-like protease nucleotide sequences of the invention, and fragments and variants thereof, can be used as probes and/or primers to identify and/or clone calpain-like protease homologs in other cell types, e.g., from other tissues, as well as calpain-like protease homologs from other mammals. Such probes can be used to detect transcripts or genomic sequences encoding the same or identical proteins. These probes can be used as part of a diagnostic test kit for identifying cells or tissues that misexpress a calpain-like protease protein, such as by measuring levels of a calpain-like protease-encoding nucleic acid in a sample of cells from a subject, e.g., detecting calpain-like protease mRNA levels or determining whether a genomic calpain-like protease gene has been mutated or deleted.

In this manner, methods such as PCR, hybridization, and the like can be used to identify such sequences having substantial identity to the sequences of the invention. See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols: A Guide to Methods and Applications* (Academic Press, NY). Calpain-like protease nucleotide sequences isolated based on their sequence identity to the calpain-like protease nucleotide sequences set forth herein or to fragments and variants thereof are encompassed by the present invention.

In a hybridization method, all or part of a known calpain-like protease nucleotide sequence can be used to screen cDNA or genomic libraries. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.). The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor Probes for hybridization can be made by labeling synthetic oligonucleotides based on the known calpain-like protease nucleotide sequence disclosed herein. Degenerate primers designed on the basis of conserved nucleotides or amino acid residues in a known calpain-like protease nucleotide sequence or encoded amino acid sequence can additionally be used. The probe typically comprises a region of nucleotide sequence that hybridizes under stringent conditions to at least about 10, 15, preferably about 25, more preferably at least about 50, 75, 100, 125, 150, 175, 200, 250, 300, 350, or 400 consecutive nucleotides of a calpain-like protease nucleotide sequence of the invention or a fragment or variant thereof. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference.

For example, in one embodiment, a previously unidentified calpain-like protease nucleic acid molecule hybridizes under stringent conditions to a probe that is a nucleic acid molecule comprising the calpain-like protease nucleotide sequence of the invention or a fragment thereof. In another embodiment, the previously unknown calpain-like protease nucleic acid molecule is at least 300, 325, 350, 375, 400, 425, 450, 500, 550, 600, 650, 700, 800, 900, 1000, or 2000 nucleotides in length and hybridizes under stringent conditions to a probe that is a nucleic acid molecule comprising the calpain-like protease nucleotide sequence disclosed herein or a fragment thereof. The probe is derived, in one embodiment, from the coding sequence set forth in SEQ ID NO:1, SEQ ID NO:3, the cDNA insert of the plasmid deposited with ATCC as Patent Deposit Number PTA-2203, or a fragment thereof.

As used herein, the term "hybridizes under stringent conditions" describes conditions for hybridization and washing. Stringent conditions are known to those skilled in the art and can be found in Current Protocols in Molecular Biology John Wiley & Sons, N.Y. (1989), 6.3.1–6.3.6. Aqueous and nonaqueous methods are described in that reference and either can be used. A preferred, example of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions are hybridization in 6× sodium chloride/sodium citrate (SSC) at about 45° C., followed by one or more washes in 0.2×SSC, 0.1% SDS at 60° C. Preferably, stringent hybridization conditions are hybridization in 6× sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. Preferably, an isolated nucleic acid molecule of the invention that hybridizes under stringent conditions to the sequence of SEQ ID NO:1 or SEQ ID NO:3 corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

Thus, in addition to the calpain-like protease nucleotide sequences disclosed herein and fragments and variants thereof, the isolated nucleic acid molecules of the invention also encompass homologous DNA sequences identified and isolated from other cells and/or organisms by hybridization with entire or partial sequences obtained from the calpain-like protease nucleotide sequences disclosed herein or variants and fragments thereof.

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire calpain-like protease coding strand, or to only a portion thereof, e.g., all or part of the protein coding region (or open reading frame). An antisense nucleic acid molecule can be antisense to a noncoding region of the coding strand of a nucleotide sequence encoding a calpain-like protease protein. The noncoding regions are the 5' and 3' sequences that flank the coding region and are not translated into amino acids.

Given the coding-strand sequences encoding a calpain-like protease protein disclosed herein (e.g., SEQ ID NO:1 and SEQ ID NO:3), antisense nucleic acids of the invention can be designed according to the rules of Watson and Crick base pairing. The antisense nucleic acid molecule can be complementary to the entire coding region of calpain-like protease mRNA, but more preferably is an oligonucleotide that is antisense to only a portion of the coding or noncoding region of calpain-like protease mRNA. For example, the antisense oligonucleotide can be complementary to the region surrounding the translation start site of calpain-like protease mRNA. An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation procedures known in the art.

For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, including, but not limited to, for example e.g., phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a calpain-like protease protein to thereby inhibit expression of the protein, e.g., by inhibiting transcription and/or translation. An example of a route of administration of antisense nucleic acid molecules of the invention includes direct injection at a tissue site. Alternatively, antisense nucleic acid molecules can be modified to target selected cells and then administered systemically. For example, antisense molecules can be linked to peptides or antibodies to form a complex that specifically binds to receptors or antigens expressed on a selected cell surface. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention also encompasses ribozymes, which are catalytic RNA molecules with ribonuclease activity that are capable of cleaving a single-stranded nucleic acid, such as an mRNA, to which they have a complementary region. Ribozymes (e.g., hammerhead ribozymes (described in Haselhoff and Gerlach (1988) *Nature* 334:585–591)) can be used to catalytically cleave calpain-like protease mRNA transcripts to thereby inhibit translation of calpain-like protease mRNA. A ribozyme having specificity for a calpain-like protease -encoding nucleic acid can be designed based upon the nucleotide sequence of a calpain-like protease cDNA disclosed herein (e.g., SEQ ID NO:1 or SEQ ID NO:3). See, e.g., Cech et al., U.S. Pat. No. 4,987,071; and Cech et al., U.S. Pat. No. 5,116,742. Alternatively, calpain-like protease mRNA can be used to select a catalytic RNA having a specific ribonuclease activity from a pool of RNA molecules. See, e.g., Bartel and Szostak (1993) *Science* 261:1411–1418.

The invention also encompasses nucleic acid molecules that form triple helical structures. For example, calpain-like protease gene expression can be inhibited by targeting nucleotide sequences complementary to the regulatory region of the calpain-like protease protein (e.g., the calpain-like protease promoter and/or enhancers) to form triple helical structures that prevent transcription of the calpain-like protease gene in target cells. See generally Helene (1991) *Anticancer Drug Des.* 6(6):569; Helene (1992) *Ann. N.Y. Acad. Sci.* 660:27; and Maher (1992) *Bioassays* 14(12):807.

In preferred embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described in Hyrup et al. (1996), supra; Perry-O'Keefe et al. (1996) *Proc. Natl. Acad. Sci. USA* 93:14670.

PNAs of a calpain-like protease molecule can be used in therapeutic and diagnostic applications. For example, PNAs can be used as antisense or antigene agents for sequence-specific modulation of gene expression by, e.g., inducing transcription or translation arrest or inhibiting replication. PNAs of the invention can also be used, e.g., in the analysis of single base pair mutations in a gene by, e.g., PNA-directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996), supra).

In another embodiment, PNAs of a calpain-like protease molecule can be modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra; Finn et al. (1996) *Nucleic Acids Res.* 24(17):3357–63; Mag et al. (1989) *Nucleic Acids Res.* 17:5973; and Peterson et al. (1975) *Bioorganic Med. Chem. Lett.* 5:1119.

II. Isolated Calpain-like Protease Proteins and Anti-calpain-like Protease Antibodies Calpain protease proteins are also encompassed within the present invention. By "calpain-like protease protein" is intended a protein having the amino acid sequence set forth in SEQ ID NO:2, as well as fragments, biologically active portions, and variants thereof.

"Fragments" or "biologically active portions" include polypeptide fragments suitable for use as immunogens to raise anti-calpain-like protease antibodies. Fragments include peptides comprising amino acid sequences sufficiently identical to or derived from the amino acid sequence of a calpain-like protease protein, or partial-length protein, of the invention and exhibiting at least one activity of a calpain-like protease protein, but which include fewer amino acids than the full-length (SEQ ID NO:2) calpain-like protease protein disclosed herein. Typically, biologically active portions comprise a domain or motif with at least one activity of the calpain-like protease protein. A biologically active portion of a calpain-like protease protein can be a polypeptide which is, for example, 10, 25, 50, 100 or more amino acids in length. Such biologically active portions can be prepared by recombinant techniques and evaluated for one or more of the functional activities of a native calpain-like protease protein. As used here, a fragment not previously disclosed comprises at least 5 contiguous amino acids of SEQ ID NO:2. The invention encompasses other fragments, however, such as any fragment in the protein greater than 6, 7, 8, 9, 10, 11, 12, 13, 14, 15 16, 17, 18, 19, or 20 amino acids that has not been previously disclosed.

By "variants" is intended proteins or polypeptides having an amino acid sequence that is at least about 60%, 65%, or 70%, preferably about 75%, 85%, 90%, 91%, 92%, 93%, 94%, 95%, 96%, 97%, 98%, or 99% identical to the amino acid sequence of SEQ ID NO:2. Variants also include polypeptides encoded by the cDNA insert of the plasmid deposited with ATCC as Accession Number PTA-2203, or polypeptides encoded by a nucleic acid molecule that hybridizes to the nucleic acid molecule of SEQ ID NO:1, SEQ ID NO:3, or a complement thereof, under stringent conditions. In another embodiment, a variant of an isolated polypeptide of the present invention differs, by at least 1, but less than 5, 10, 20, 50, or 100 amino acid residues from the sequence shown in SEQ ID NO:2. If alignment is needed for this comparison the sequences should be aligned for maximum identity. "Looped" out sequences from deletions or insertions, or mismatches, are considered differences. Such variants generally retain the functional activity of the SEQ ID NO:2 proteins of the invention. Variants include polypeptides that differ in amino acid sequence due to natural allelic variation or mutagenesis.

The invention also provides calpain-like protease chimeric or fusion proteins. As used herein, a calpain-like protease "chimeric protein" or "fusion protein" comprises a calpain-like protease polypeptide operably linked to a non-calpain-like protease polypeptide. A "calpain-like protease polypeptide" refers to a polypeptide having an amino acid sequence corresponding to a calpain-like protease protein, whereas a "non-calpain-like protease polypeptide" refers to a polypeptide having an amino acid sequence corresponding to a protein that is not substantially identical to the calpain-like protease protein, e.g., a protein that is different from the calpain-like protease protein and which is derived from the same or a different organism. Within a calpain-like protease fusion protein, the calpain-like protease polypeptide can correspond to all or a portion of a calpain-like protease protein, preferably at least one biologically active portion of a calpain-like protease protein. Within the fusion protein, the term "operably linked" is intended to indicate that the calpain-like protease polypeptide and the non-calpain-like protease polypeptide are fused in-frame to each other. The non-calpain-like protease polypeptide can be fused to the N-terminus or C-terminus of the calpain-like protease polypeptide.

One useful fusion protein is a GST-calpain-like protease fusion protein in which the calpain-like protease sequences are fused to the N- or C-terminus of the GST sequences. Such fusion proteins can facilitate the purification of recombinant calpain-like protease proteins.

In yet another embodiment, the fusion protein is a calpain-like protease-immunoglobulin fusion protein in which all or part of a calpain-like protease protein is fused to sequences derived from a member of the immunoglobulin protein family. The calpain-like protease-immunoglobulin fusion proteins of the invention can be incorporated into pharmaceutical compositions and administered to a subject to inhibit an interaction between a calpain-like protease ligand and a calpain-like protease protein on the surface of a cell, thereby suppressing calpain-like protease-mediated signal transduction in vivo. The calpain-like protease-immunoglobulin fusion proteins can be used to affect the bioavailability of a calpain-like protease cognate ligand. Inhibition of the calpain-like protease ligand/calpain-like protease interaction may be useful therapeutically, both for treating proliferative and differentiative disorders and for modulating (e.g., promoting or inhibiting) cell survival. Moreover, the calpain-like protease-immunoglobulin fusion proteins of the invention can be used as immunogens to produce anti-calpain-like protease antibodies in a subject, to purify calpain-like protease ligands, and in screening assays to identify molecules that inhibit the interaction of a calpain-like protease protein with a calpain-like protease ligand.

Preferably, a calpain-like protease chimeric or fusion protein of the invention is produced by standard recombinant DNA techniques. For example, DNA fragments coding for the different polypeptide sequences may be ligated together in-frame, or the fusion gene can be synthesized, such as with automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (see, e.g., Ausubel et al., eds. (1995) *Current Protocols in Molecular Biology*) (Greene Publishing and Wiley-Interscience, NY). Moreover, a calpain-like protease-encoding nucleic acid can be cloned into a commercially available expression vector such that it is linked in-frame to an existing fusion moiety.

Variants of the calpain-like protease proteins can function as either calpain-like protease agonists (mimetics) or as calpain-like protease antagonists. Variants of the calpain-like protease protein can be generated by mutagenesis, e.g., discrete point mutation or truncation of the calpain-like protease protein. An agonist of the calpain-like protease protein can retain substantially the same, or a subset, of the biological activities of the naturally occurring form of the calpain-like protease protein. An antagonist of the calpain-like protease protein can inhibit one or more of the activities of the naturally occurring form of the calpain-like protease protein by, for example, competitively binding to a downstream or upstream member of a cellular signaling cascade that includes the calpain-like protease protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the calpain-like protease proteins.

Variants of a calpain-like protease protein that function as either calpain-like protease agonists or as calpain-like protease antagonists can be identified by screening combinatorial libraries of mutants, e.g., truncation mutants, of a calpain-like protease protein for calpain-like protease protein agonist or antagonist activity. In one embodiment, a variegated library of calpain-like protease variants is generated by combinatorial mutagenesis at the nucleic acid level and is encoded by a variegated gene library. A variegated library of calpain-like protease variants can be produced by, for example, enzymatically ligating a mixture of synthetic oligonucleotides into gene sequences such that a degenerate set of potential calpain-like protease sequences is expressible as individual polypeptides, or alternatively, as a set of larger fusion proteins (e.g., for phage display) containing the set of calpain-like protease sequences therein. There are a variety of methods that can be used to produce libraries of potential calpain-like protease variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential calpain-like protease sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of a calpain-like protease protein coding sequence can be used to generate a variegated population of calpain-like protease fragments for screening and subsequent selection of variants of a calpain-like protease protein. In one embodiment, a library of coding sequence fragments can be generated by treating a double-stranded PCR fragment of a calpain-like protease coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the calpain-like protease protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of calpain-like protease proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify calpain-like protease variants (Arkin and Yourvan (1992) *Proc. Natl. Acad. Sci. USA* 89:7811–7815; Delgrave et al. (1993) *Protein Engineering* 6(3):327–331).

An isolated calpain-like protease polypeptide of the invention can be used as an immunogen to generate antibodies that bind calpain-like protease proteins using standard techniques for polyclonal and monoclonal antibody preparation. The full-length calpain-like protease protein can be used or, alternatively, the invention provides antigenic peptide fragments of calpain-like protease proteins for use as immunogens. The antigenic peptide of a calpain-like protease protein comprises at least 8, preferably 10, 15, 20, or 30 amino acid residues of the amino acid sequence shown in SEQ ID NO:2 and encompasses an epitope of a calpain-like protease protein such that an antibody raised against the peptide forms a specific immune complex with the calpain-like protease protein. Preferred epitopes encompassed by the antigenic peptide are regions of a calpain-like protease protein that are located on the surface of the protein, e.g., hydrophilic regions.

Accordingly, another aspect of the invention pertains to anti-calpain-like protease polyclonal and monoclonal antibodies that bind a calpain-like protease protein. Polyclonal anti-calpain-like protease antibodies can be prepared by immunizing a suitable subject (e.g., rabbit, goat, mouse, or other mammal) with a calpain-like protease immunogen. The anti-calpain-like protease antibody titer in the immunized subject can be monitored over time by standard techniques, such as with an enzyme linked immunosorbent assay (ELISA) using immobilized calpain-like protease protein. At an appropriate time after immunization, e.g., when the anti-calpain-like protease antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985) in *Monoclonal Antibodies and Cancer Therapy,* ed. Reisfeld and Sell (Alan R. Liss, Inc., New York, N.Y.), pp. 77–96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:550–52; Kenneth (1980) in *Monoclonal Antibodies: A New Dimension In Biological Analyses* (Plenum Publishing Corp., NY; and Lerner (1981) *Yale J. Biol. Med.,* 54:387–402).

Alternative to preparing monoclonal antibody-secreting hybridomas, a monoclonal anti-calpain-like protease antibody can be identified and isolated by screening a recombinant combinatorial immunoglobulin library (e.g., an antibody phage display library) with a calpain-like protease protein to thereby isolate immunoglobulin library members that bind the calpain-like protease protein. Kits for generating and screening phage display libraries are commercially available (e.g., the Pharmacia *Recombinant Phage Antibody System,* Catalog No. 27–9400–01; and the Stratagene *SurfZAP™ Phage Display Kit,* Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

Additionally, recombinant anti-calpain-like protease antibodies, such as chimeric and humanized monoclonal antibodies, comprising both human and nonhuman portions, which can be made using standard recombinant DNA techniques, are within the scope of the invention. Such chimeric and humanized monoclonal antibodies can be produced by recombinant DNA techniques known in the art, for example using methods described in PCT Publication Nos. WO 86/01533 and WO 87/02671; European Patent Application Nos. 184,187, 171,496, 125,023, and 173,494; U.S. Pat. Nos. 4,816,567 and 5,225,539; European Patent Application 125,023; Better et al. (1988) *Science* 240:1041–1043; Liu et at. (1987) *Proc. Natl. Acad. Sci. USA* 84:3439–3443, Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; Shaw et al. (1988) *J. Natl. Cancer Inst.* 80:1553–1559); Morrison (1985) *Science* 229:1202–1207; Oi et al. (1986) *Bio/Techniques* 4:214; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65–93); and U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies that recognize a selected epitope can be generated using a technique referred to as "guided selection." In this approach, a selected non-human monoclonal antibody, e.g., a murine antibody, is used to guide the selection of a completely human antibody recognizing the same epitope. This technology is described by Jespers et al. (1994) *Bio/Technology* 12:899–903).

An anti-calpain-like protease antibody (e.g., monoclonal antibody) can be used to isolate calpain-like protease proteins by standard techniques, such as affinity chromatography or immunoprecipitation. An anti-calpain-like protease antibody can facilitate the purification of natural calpain-like protease protein from cells and of recombinantly produced calpain-like protease protein expressed in host cells. Moreover, an anti-calpain-like protease antibody can be used to detect calpain-like protease protein (e.g., in a cellular lysate or cell supernatant) in order to evaluate the abundance and pattern of expression of the calpain-like protease protein. Anti-calpain-like protease antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

III. Recombinant Expression Vectors and Host Cells

Another aspect of the invention pertains to vectors, preferably expression vectors, containing a nucleic acid encoding a calpain-like protease protein (or a portion thereof). "Vector" refers to a nucleic acid molecule capable of transporting another nucleic acid to which it has been linked, such as a "plasmid", a circular double-stranded DNA loop into which additional DNA segments can be ligated, or a viral vector, where additional DNA segments can be ligated into the viral genome. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses, and adeno-associated viruses), that serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, operably linked to the nucleic acid sequence to be expressed. "Operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., calpain-like protease proteins, mutant forms of calpain-like protease proteins, fusion proteins, etc.).

The recombinant expression vectors of the invention can be designed for expression of calpain-like protease protein in prokaryotic or eukaryotic host cells. Expression of proteins in prokaryotes is most often carried out in *E. coli* with vectors containing constitutive or inducible promoters directing the expression of either fusion or nonfusion proteins. Fusion vectors add a number of amino acids to a protein encoded therein, usually to the amino terminus of the recombinant protein. Typical fusion expression vectors include pGEX (Pharmacia Biotech Inc. Smith and Johnson (1988) *Gene* 67:31–40), pMAL (New England Biolabs, Beverly, Mass.), and pRIT5 (Pharmacia, Piscataway, N.J.) which fuse glutathione S-transferase (GST), maltose E binding protein, or protein A, respectively, to the target recombinant protein. Examples of suitable inducible nonfusion *E. coli* expression vectors include pTrc (Amann et al. (1988) *Gene* 69:301–315) and pET 11d (Studier et al. (1990) in *Gene Expression Technology: Methods in Enzymology* 185 (Academic Press, San Diego, Calif.), pp. 60–89). Strategies to maximize recombinant protein expression in *E. coli* can be found in Gottesman (1990) in *Gene Expression Technology: Methods in Enzymology* 185 (Academic Press, Calif.), pp. 119–128 and Wada et al. (1992) *Nucleic Acids Res.* 20:2111–2118. Target gene expression from the pTrc vector relies on host RNA polymerase transcription from a hybrid trp-lac fusion promoter.

Suitable eukaryotic host cells include insect cells (examples of Baculovirus vectors available for expression of proteins in cultured insect cells (e.g., Sf9 cells) include the pAc series (Smith et al. (1983) *Mol. Cell Biol.* 3:2156–2165) and the pVL series (Lucklow and Summers (1989) *Virology* 170:31–39)); yeast cells (examples of vectors for expression in yeast *S. cereivisiae* include pYepSec1 (Baldari et al. (1987) *EMBO J.* 6:229–234), pMFa (Kuijan and Herskowitz (1982) *Cell* 30:933–943), pJRY88 (Schultz et al. (1987) *Gene* 54:113–123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) *Nature* 329:840) and pMT2PC (Kaufman et al. (1987) *EMBO J.* 6:187:195)). Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook et al. (1989) *Molecular cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.). Alternatively, the recombinant expression vector can be transcribed and translated in vitro, for example using T7 promoter regulatory sequences and T7 polymerase.

It is further recognized that the nucleic acid sequences of the invention can be altered to contain codons, which are preferred, or non preferred, for a particular expression system. For example, the nucleic acid can be one in which at least one altered codon, and preferably at least 10%, or 20% of the codons have been altered such that the sequence is optimized for expression in *E. coli,* yeast, human, insect, or CHO cells. Methods for determining such codon usage are well known in the art.

The terms "host cell" and "recombinant host cell" are used interchangeably herein It is understood that such terms refer not only to the particular subject cell but to the progeny or potential progeny of such a cell. Because certain modifications may occur in succeeding generations due to either mutation or environmental influences, such progeny may not, in fact, be identical to the parent cell but are still included within the scope of the term as used herein.

In one embodiment, the expression vector is a recombinant mammalian expression vector that comprises tissue-specific regulatory elements that direct expression of the nucleic acid preferentially in a particular cell type. Suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Baneiji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Patent Publication No. 264, 166). Developmentally-regulated promoters are also encompassed, for example the murine hox promoters (Kessel and Gruss (1990) *Science* 249:374–379), the α-fetoprotein promoter (Campes and Tilghman (1989) *Genes Dev.* 3:537–546), and the like.

The invention further provides a recombinant expression vector comprising a DNA molecule of the invention cloned into the expression vector in an antisense orientation. That is, the DNA molecule is operably linked to a regulatory sequence in a manner that allows for expression (by transcription of the DNA molecule) of an RNA molecule that is antisense to calpain-like protease mRNA. Regulatory sequences operably linked to a nucleic acid cloned in the antisense orientation can be chosen to direct the continuous expression of the antisense RNA molecule in a variety of cell types, for instance viral promoters and/or enhancers, or regulatory sequences can be chosen to direct constitutive, tissue-specific, or cell-type-specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986) *Reviews—Trends in Genetics,* Vol. 1(1).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboratory Manual* (2d ed., Cold Spring Harbor Laboratory Press, Plainview, N.Y.) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin, and methotrexate. Nucleic acid encoding a selectable marker can be introduced into a host cell on the same vector as that encoding a calpain-like protease protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) calpain-like protease protein. Accordingly, the invention further provides methods for producing calpain-like protease protein using the host cells of the invention. In one embodiment, the method comprises culturing the host cell of the invention, into which a recombinant expression vector encoding a calpain-like protease protein has been introduced, in a suitable medium such that calpain-like protease protein is produced. In another embodiment, the method further comprises isolating calpain-like protease protein from the medium or the host cell.

The host cells of the invention can also be used to produce nonhuman transgenic animals. For example, in one embodiment, a host cell of the invention is a fertilized oocyte or an embryonic stem cell into which calpain-like protease-coding sequences have been introduced. Such host cells can then be used to create nonhuman transgenic animals in which exogenous calpain-like protease sequences have been introduced into their genome or homologous recombinant animals in which endogenous calpain-like protease sequences have been altered. Such animals are useful for studying the function and/or activity of calpain-like protease genes and proteins and for identifying and/or evaluating modulators of calpain-like protease activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA that is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous calpain-like protease gene has been altered by homologous recombination between the endogenous gene and an exogenous DNA molecule introduced into a cell of the animal, e.g., an embryonic cell of the animal, prior to development of the animal.

A transgenic animal of the invention can be created by introducing calpain-like protease-encoding nucleic acid into the male pronuclei of a fertilized oocyte, e.g., by microinjection, retroviral infection, and allowing the oocyte to develop in a pseudopregnant female foster animal. The calpain-like protease cDNA sequence can be introduced as a transgene into the genome of a nonhuman animal. Alternatively, a homolog of the mouse calpain-like protease gene can be isolated based on hybridization and used as a transgene. Intronic sequences and polyadenylation signals can also be included in the transgene to increase the efficiency of expression of the transgene. A tissue-specific regulatory sequence(s) can be operably linked to the calpain-like protease transgene to direct expression of calpain-like protease protein to particular cells. Methods for generating transgenic animals via embryo manipulation and microinjection, particularly animals such as mice, have become conventional in the art and are described, for example, in U.S. Pat. Nos. 4,736,866, 4,870,009, and 4,873,191 and in Hogan (1986) *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the calpain-like protease transgene in its genome and/or expression of calpain-like protease mRNA in tissues or cells of the animals. A transgenic founder animal can then be used to breed additional animals carrying the transgene. Moreover, transgenic animals carrying a transgene encoding calpain-like protease gene can further be bred to other transgenic animals carrying other transgenes.

To create a homologous recombinant animal, one prepares a vector containing at least a portion of a calpain-like protease gene or a homolog of the gene into which a deletion, addition, or substitution has been introduced to thereby alter, e.g., functionally disrupt, the calpain-like protease gene. In a preferred embodiment, the vector is designed such that, upon homologous recombination, the endogenous calpain-like protease gene is functionally disrupted (i.e., no longer encodes a functional protein; also referred to as a "knock out" vector). Alternatively, the vector can be designed such that, upon homologous recombination, the endogenous calpain-like protease gene is mutated or otherwise altered but still encodes functional protein (e.g., the upstream regulatory region can be altered to thereby alter the expression of the endogenous calpain-like protease protein). In the homologous recombination vector, the altered portion of the calpain-like protease gene is flanked at its 5' and 3' ends by additional nucleic acid of the calpain-like protease gene to allow for homologous recombination to occur between the exogenous calpain-like protease gene carried by the vector and an endogenous calpain-like protease gene in an embryonic stem cell. The additional flanking calpain-like protease nucleic acid is of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors) The vector is introduced into an embryonic stem cell line (e.g., by electroporation), and cells in which the introduced calpain-like protease gene has homologously recombined with the endogenous calpain-like protease gene are selected (see, e.g., Li et al. (1992) *Cell* 69:915). The selected cells are then injected into a blastocyst of an animal (e.g., a mouse) to form aggregation chimeras (see, e.g., Bradley (1987) in *Teratocarcinomas and Embryonic Stem Cells: A Practical Approach,* ed. Robertson (IRL, Oxford pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

In another embodiment, transgenic nonhuman animals containing selected systems that allow for regulated expression of the transgene can be produced. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut et al. (1997) *Nature* 385: 810–813 and PCT Publication Nos. WO 97/07668 and WO 97/07669.

IV. Pharmaceutical Compositions

The calpain-like protease nucleic acid molecules, calpain-like protease proteins, and anti-calpain-like protease antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ brand excipient (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound (e.g., a calpain-like protease protein or anti-calpain-like protease antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch, a lubricant such as magnesium stearate or Sterotes, a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 $\mu$g/kg to about 15 mg/kg (e.g., 0.1 to 20 mg/kg) of antibody is an initial candidate dosage for administration to the patient, whether, for example, by one or more separate administrations, or by continuous infusion. A typical daily dosage might range from about 1 $\mu$g/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologs, and antibodies described herein can be used in one or more of the following methods: (a) screening assays; (b) detection assays (e.g., chromosomal mapping, tissue typing, forensic biology); (c) predictive medicine (e.g., diagnostic assays, prognostic assays, monitoring clinical trials, and pharmacogenomics); and (d) methods of treatment (e.g., therapeutic and prophylactic). The isolated nucleic acid molecules of the invention can be used to express calpain-like protease protein (e.g., via a recombinant expression vector in a host cell in gene therapy applications), to detect calpain-like protease mRNA (e.g., in a biological sample) or a genetic lesion in a calpain-like protease gene, and to modulate calpain-like protease activity. In addition, the calpain-like protease proteins can be used to screen drugs or compounds that modulate the immune response as well as to treat disorders characterized by insufficient or excessive production of calpain-like protease protein or production of calpain-like protease protein forms that have decreased or aberrant activity compared to calpain-like protease wild type protein. In addition, the anti-calpain-like protease antibodies of the invention can be used to detect and isolate calpain-like protease proteins and modulate calpain-like protease activity.

"Treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. "Subject", as used herein, can refer to a mammal, e.g. a human, or to an experimental or animal or disease model. The subject can also be a non-human animal, e.g. a horse, cow, goat, or other domestic animal. A therapeutic agent includes, but is not limited to, small molecules, peptides, antibodies, ribozymes and antisense oligonucleotides.

Figure 9:
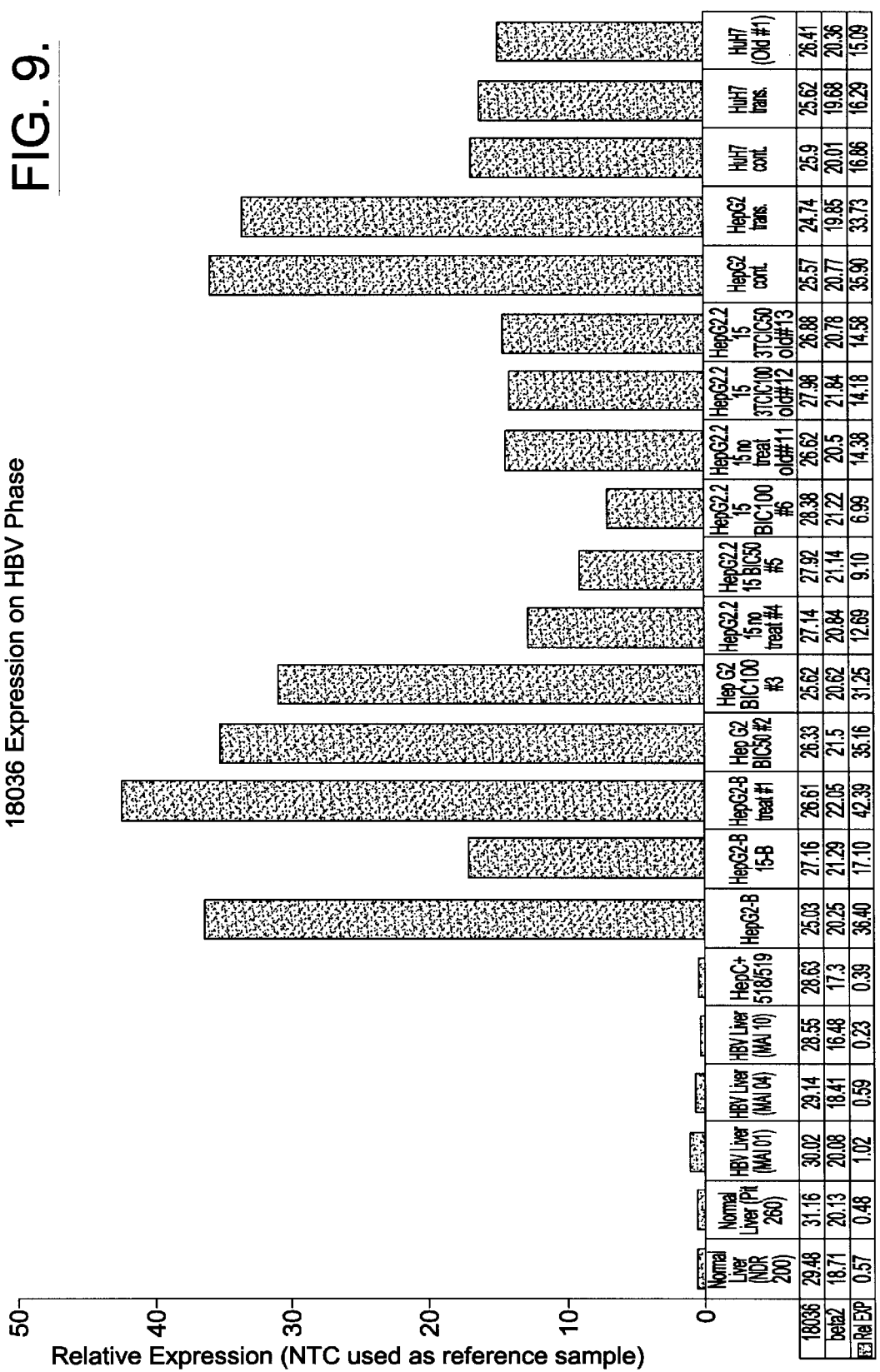
FIG. 9 shows the expression of 18036 in normal and hepatitis B (HBV) or C infected liver samples, as well has HepG2 and HuH7 cells infected or transfected with HBV. Also shown are HepG2 cells and hepatitis B-infected HepG2 cells (HepG2.2.15) that have been treated with a 50% inhibitory concentration (IC50) or 100% inhibitory concentration (IC100) of the anti-HBV drug 3TC (lamivudine). Expression levels of 18036 in various tissue and cell types were determined by quantitative RT-PCR (Reverse Transcriptase Polymerase Chain Reaction; Taqman® brand PCR kit, Applied Biosystems). The quantitative RT-PCR reactions were performed according to the kit manufacturer's instructions.

The uses and methods of the invention apply particularly to the uses and methods in tissues in which expression of the calpain-like protease occurs in tissues including, but not limited to, normal tissue from those tissues and cell lines shown in FIGS. 6 and 9 and especially those tissues in which the gene is highly expressed, for example, thyroid, spleen, lymph node, esophagus, breast, brain and aorta. In addition, expression has been observed in lymphocytes and in neural tissue including spinal cord and striatum. Accordingly, the methods and uses apply particularly to these tissues and to disorders involving these tissues.

Disorders involving the spleen include, but are not limited to, splenomegaly, including nonspecific acute splenitis, congestive spenomegaly, and spenic infarcts; neoplasms, congenital anomalies, and rupture. Disorders associated with splenomegaly include infections, such as nonspecific splenitis, infectious mononucleosis, tuberculosis, typhoid fever, brucellosis, cytomegalovirus, syphilis, malaria, histoplasmosis, toxoplasmosis, kala-azar, trypanosomiasis, schistosomiasis, leishmaniasis, and echinococcosis; congestive states related to partial hypertension, such as cirrhosis of the liver, portal or splenic vein thrombosis, and cardiac failure; lymphohematogenous disorders, such as Hodgkin disease, non-Hodgkin lymphomas/leukemia, multiple myeloma, myeloproliferative disorders, hemolytic anemias, and thrombocytopenic purpura; immunologic-inflammatory conditions, such as rheumatoid arthritis and systemic lupus erythematosus, storage diseases such as Gaucher disease, Niemann-Pick disease, and mucopolysaccharidoses; and other conditions, such as amyloidosis, primary neoplasms and cysts, and secondary neoplasms.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), *Bronchiolitis obliterans*-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors, pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A–E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, a1-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders involving the uterus and endometrium include, but are not limited to, endometrial histology in the menstrual cycle; functional endometrial disorders, such as anovulatory cycle, inadequate luteal phase, oral contraceptives and induced endometrial changes, and menopausal and postmenopausal changes; inflammations, such as chronic endometritis; adenomyosis; endometriosis; endometrial polyps; endometrial hyperplasia; malignant tumors, such as carcinoma of the endometrium; mixed Müllerian and mesenchymal tumors, such as malignant mixed Müllerian tumors; tumors of the myometrium, including leiomyomas, leiomyosarcomas, and endometrial stromal tumors.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, *Herpes simplex* virus Type 1, *Herpes simplex* virus Type 2, *Varicalla-zoster* virus (*Herpes zoster*), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving T-cells include, but are not limited to, cell-mediated hypersensitivity, such as delayed type hypersensitivity and T-cell-mediated cytotoxicity, and transplant rejection; autoimmune diseases, such as systemic lupus erythematosus, Sjögren syndrome, systemic sclerosis, inflammatory myopathies, mixed connective tissue disease, and polyarteritis nodosa and other vasculitides; immunologic deficiency syndromes, including but not limited to, primary immunodeficiencies, such as thymic hypoplasia, severe combined immunodeficiency diseases, and AIDS; leukopenia; reactive (inflammatory) proliferations of white cells, including but not limited to, leukocytosis, acute nonspecific lymphadenitis, and chronic nonspecific lymphadenitis; neoplastic proliferations of white cells, including but not limited to lymphoid neoplasms, such as precursor T-cell neoplasms, such as acute lymphoblastic leukemia/lymphoma, peripheral T-cell and natural killer cell neoplasms that include peripheral T-cell lymphoma, unspecified, adult T-cell leukemia/lymphoma, mycosis fungoides and Sézary syndrome, and Hodgkin disease.

Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors, tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

In normal bone marrow, the myelocytic series (polymorphoneuclear cells) make up approximately 60% of the cellular elements, and the erythrocytic series, 20–30%. Lymphocytes, monocytes, reticular cells, plasma cells and megakaryocytes together constitute 10–20%. Lymphocytes make up 5–15% of normal adult marrow. In the bone marrow, cell types are add mixed so that precursors of red blood cells (erythroblasts), macrophages (monoblasts), platelets (megakaryocytes), polymorphoneuclear leucocytes (myeloblasts), and lymphocytes (lymphoblasts) can be visible in one microscopic field. In addition, stem cells exist for the different cell lineages, as well as a precursor stem cell for the committed progenitor cells of the different lineages. The various types of cells and stages of each would be known to the person of ordinary skill in the art and are found, for example, on page 42 (FIGS. 2–8) of *Immunology, Imunopathology and Immunity*, Fifth Edition, Sell et al. Simon and Schuster (1996), incorporated by reference for its teaching of cell types found in the bone marrow. According, the invention is directed to disorders arising from these cells. These disorders include but are not limited to the following: diseases involving hematopoeitic stem cells; committed lymphoid progenitor cells; lymphoid cells including B and T-cells; committed myeloid progenitors, including monocytes, granulocytes, and megakaryocytes; and committed erythroid progenitors. These include but are not limited to the leukemias, including B-lymphoid leukemias, T-lymphoid leukemias, undifferentiated leukemias; erythroleukemia, megakaryoblastic leukemia, monocytic; [leukemias are encompassed with and without differentiation]; chronic and acute lymphoblastic leukemia, chronic and acute lymphocytic leukemia, chronic and acute myelogenous leukemia, lymphoma, myelo dysplastic syndrome, chronic and acute myeloid leukemia, myelomonocytic leukemia; chronic and acute myeloblastic leukemia, chronic and acute myelogenous leukemia, chronic and acute promyelocytic leukemia, chronic and acute myelocytic leukemia, hematologic malignancies of monocyte-macrophage lineage, such as juvenile chronic myelogenous leukemia; secondary AML, antecedent hematological disorder; refractory anemia; aplastic anemia; reactive cutaneous angioendotheliomatosis; fibrosing disorders involving altered expression in dendritic cells, disorders including systemic sclerosis, E-M syndrome, epidemic toxic oil syndrome, eosinophilic fasciitis localized forms of scleroderma, keloid, and fibrosing colonopathy; angiomatoid malignant fibrous histiocytoma; carcinoma, including primary head and neck squamous cell carcinoma; sarcoma, including kaposi's sarcoma; fibroadanoma and phyllodes tumors, including mammary fibroadenoma; stromal tumors; phyllodes tumors, including histiocytoma; erythroblastosis; neurofibromatosis; diseases of the vascular endothelium; demyelinating, particularly in old lesions; gliosis, vasogenic edema, vascular disease, Alzheimer's and Parkinson's disease; T-cell lymphomas; B-cell lymphomas.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders involving red cells include, but are not limited to, anemias, such as hemolytic anemias, including hereditary spherocytosis, hemolytic disease due to erythrocyte enzyme defects: glucose-6-phosphate dehydrogenase deficiency, sickle cell disease, thalassemia syndromes, paroxysmal nocturnal hemoglobinuria, immunohemolytic anemia, and hemolytic anemia resulting from trauma to red cells; and anemias of diminished erythropoiesis, including megaloblastic anemias, such as anemias of vitamin $B_{12}$ deficiency: pernicious anemia, and anemia of folate deficiency, iron deficiency anemia, anemia of chronic disease, aplastic anemia, pure red cell aplasia, and other forms of marrow failure.

Disorders involving the thymus include developmental disorders, such as DiGeorge syndrome with thymic hypoplasia or aplasia; thymic cysts; thymic hypoplasia, which involves the appearance of lymphoid follicles within the thymus, creating thymic follicular hyperplasia; and thymomas, including germ cell tumors, lymphomas, Hodgkin disease, and carcinoids. Thymomas can include benign or encapsulated thymoma, and malignant thymoma Type I (invasive thymoma) or Type II, designated thymic carcinoma.

Disorders involving B-cells include, but are not limited to precursor B-cell neoplasms, such as lymphoblastic leukemia/lymphoma. Peripheral B-cell neoplasms include, but are not limited to, chronic lymphocytic leukemia/small lymphocytic lymphoma, follicular lymphoma, diffuse large B-cell lymphoma, Burkitt lymphoma, plasma cell neoplasms, multiple myeloma, and related entities, lymphoplasmacytic lymphoma (Waldenström macroglobulinemia), mantle cell lymphoma, marginal zone lymphoma (MALToma), and hairy cell leukemia.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Disorders of the breast include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms.

Disorders in the male breast include, but are not limited to, gynecomastia and carcinoma.

Disorders involving the testis and epididymis include, but are not limited to, congenital anomalies such as cryptorchidism, regressive changes such as atrophy, inflammations such as nonspecific epididymitis and orchitis, granulomatous (autoimmune) orchitis, and specific inflammations including, but not limited to, gonorrhea, mumps, tuberculosis, and syphilis, vascular disturbances including torsion, testicular tumors including germ cell tumors that include, but are not limited to, seminoma, spermatocytic seminoma, embryonal carcinoma, yolk sac tumor choriocarcinoma, teratoma, and mixed tumors, tumors of sex cord-gonadal stroma including, but not limited to, Leydig (interstitial) cell tumors and sertoli cell tumors (androblastoma), and testicular lymphoma, and miscellaneous lesions of tunica vaginalis.

Disorders involving the prostate include, but are not limited to, inflammations, benign enlargement, for example, nodular hyperplasia (benign prostatic hypertrophy or hyperplasia), and tumors such as carcinoma.

Disorders involving the thyroid include, but are not limited to, hyperthyroidism; hypothyroidism including, but not limited to, cretinism and myxedema; thyroiditis including, but not limited to, hashimoto thyroiditis, subacute (granulomatous) thyroiditis, and subacute lymphocytic (painless) thyroiditis; Graves disease; diffuse and multinodular goiter including, but not limited to, diffuse nontoxic (simple) goiter and multinodular goiter; neoplasms of the thyroid including, but not limited to, adenomas, other benign tumors, and carcinomas, which include, but are not limited to, papillary carcinoma, follicular carcinoma, medullary carcinoma, and anaplastic carcinoma; and cogenital anomalies.

Disorders involving the skeletal muscle include tumors such as rhabdomyosarcoma.

Disorders involving the pancreas include those of the exocrine pancreas such as congenital anomalies, including but not limited to, ectopic pancreas; pancreatitis, including but not limited to, acute pancreatitis, cysts, including but not limited to, pseudocysts; tumors, including but not limited to, cystic tumors and carcinoma of the pancreas; and disorders of the endocrine pancreas such as, diabetes mellitus; islet cell tumors, including but not limited to, insulinomas, gastrinomas, and other rare islet cell tumors.

Disorders involving the small intestine include the malabsorption syndromes such as, celiac sprue, tropical sprue (postinfectious sprue), whipple disease, disaccharidase (lactase) deficiency, abetalipoproteinemia, and tumors of the small intestine including adenomas and adenocarcinoma.

Disorders related to reduced platelet number, thrombocytopenia, include idiopathic thrombocytopenic purpura, including acute idiopathic thrombocytopenic purpura, drug-induced thrombocytopenia, HIV-associated thrombocytopenia, and thrombotic microangiopathies: thrombotic thrombocytopenic purpura and hemolytic-uremic syndrome.

Disorders involving precursor T-cell neoplasms include precursor T lymphoblastic leukemia/lymphoma. Disorders involving peripheral T-cell and natural killer cell neoplasms include T-cell chronic lymphocytic leukemia, large granular lymphocytic leukemia, mycosis fungoides and Sézary syndrome, peripheral T-cell lymphoma, unspecified, angio-immunoblastic T-cell lymphoma, angiocentric lymphoma (NK/T-cell lymphoma[4a]), intestinal T-cell lymphoma, adult T-cell leukemia/lymphoma, and anaplastic large cell lymphoma.

Disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

Bone-forming cells include the osteoprogenitor cells, osteoblasts, and osteocytes. The disorders of the bone are complex because they may have an impact on the skeleton during any of its stages of development. Hence, the disorders may have variable manifestations and may involve one, multiple or all bones of the body. Such disorders include, congenital malformations, achondroplasia and thanatophoric dwarfism, diseases associated with abnormal matix such as type 1 collagen disease, osteoporosis, Paget disease, rickets, osteomalacia, high-turnover osteodystrophy, low-turnover of aplastic disease, osteonecrosis, pyogenic osteomyelitis, tuberculous osteomyelitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, Ewing sarcoma, primitive neuroectodermal tumor, giant cell tumor, and metastatic tumors.

A. Screening Assays

The invention provides a method (also referred to herein as a "screening assay") for identifying modulators, i.e., candidate or test compounds or agents (e.g., peptides, peptidomimetics, small molecules, or other drugs) that bind to calpain-like protease proteins or have a stimulatory or inhibitory effect on, for example, calpain-like protease expression or calpain-like protease activity.

The test compounds of the present invention can be obtained using any of the numerous approaches in combinatorial library methods known in the art, including biological libraries, spatially addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865–1869), or phage (Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

Determining the ability of the test compound to bind to the calpain-like protease protein can be accomplished, for example, by coupling the test compound with a radioisotope or enzymatic label such that binding of the test compound to the calpain-like protease protein or biologically active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radio emission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In a similar manner, one may determine the ability of the calpain-like protease protein to bind to or interact with a calpain-like protease target molecule. By "target molecule" is intended a molecule with which a calpain-like protease protein binds or interacts in nature. In a preferred embodiment, the ability of the calpain-like protease protein to bind to or interact with a calpain-like protease target molecule can be determined by monitoring the activity of the target molecule. For example, the activity of the target molecule can be monitored by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a calpain-like protease -responsive regulatory element operably linked to a nucleic acid encoding a detectable marker, e.g. luciferase), or detecting a cellular response, for example, cellular differentiation or cell proliferation.

In yet another embodiment, an assay of the present invention is a cell-free assay comprising contacting a calpain-like protease protein or biologically active portion thereof with a test compound and determining the ability of the test compound to bind to the calpain-like protease protein or biologically active portion thereof Binding of the test compound to the calpain-like protease protein can be determined either directly or indirectly as described above. In a preferred embodiment, the assay includes contacting the calpain-like protease protein or biologically active portion thereof with a known compound that binds calpain-like protease protein to form an assay mixture, contacting the assay mixture with a test compound, and determining the ability of the test compound to preferentially bind to calpain-like protease protein or biologically active portion thereof as compared to the known compound.

In another embodiment, an assay is a cell-free assay comprising contacting calpain-like protease protein or biologically active portion thereof with a test compound and determining the ability of the test compound to modulate (e.g. stimulate or inhibit) the activity of the calpain-like protease protein or biologically active portion thereof. Determining the ability of the test compound to modulate the activity of a calpain-like protease protein can be accomplished, for example, by determining the ability of the calpain-like protease protein to bind to a calpain-like protease target molecule as described above for determining direct binding. In an alternative embodiment, determining the ability of the test compound to modulate the activity of a calpain-like protease protein can be accomplished by determining the ability of the calpain-like protease protein to further modulate a calpain-like protease target molecule. For example, the catalytic/enzymatic activity of the target molecule on an appropriate substrate can be determined as previously described.

In yet another embodiment, the cell-free assay comprises contacting the calpain-like protease protein or biologically active portion thereof with a known compound that binds a calpain-like protease protein to form an assay mixture, contacting the assay mixture with a test compound, and determining the ability of the test compound to preferentially bind to or modulate the activity of a calpain-like protease target molecule.

In the above-mentioned assays, it may be desirable to immobilize either a calpain-like protease protein or its target molecule to facilitate separation of complexed from uncomplexed forms of one or both of the proteins, as well as to accommodate automation of the assay. In one embodiment, a fusion protein can be provided that adds a domain that allows one or both of the proteins to be bound to a matrix. For example, glutathione-S-transferase/calpain-like protease fusion proteins or glutathione-S-transferase/target fusion proteins can be adsorbed onto glutathione sepharose beads (Sigma Chemical, St. Louis, Mo.) or glutathione-derivatized microtitre plates, which are then combined with the test compound or the test compound and either the nonadsorbed target protein or calpain-like protease protein, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of calpain-like protease binding or activity determined using standard techniques.

Other techniques for immobilizing proteins on matrices can also be used in the screening assays of the invention. For example, either calpain-like protease protein or its target molecule can be immobilized utilizing conjugation of biotin and streptavidin. Biotinylated calpain-like protease molecules or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96-well plates (Pierce Chemicals). Alternatively, antibodies reactive with a calpain-like protease protein or target molecules but which do not interfere with binding of the calpain-like protease protein to its target molecule can be derivatized to the wells of the plate, and unbound target or calpain-like protease protein trapped in the wells by antibody conjugation. Methods for detecting such complexes, in addition to those described above for the GST-immobilized complexes, include immunodetection of complexes using antibodies reactive with the calpain-like protease protein or target molecule, as well as enzyme-linked assays that rely on detecting an enzymatic activity associated with the calpain-like protease protein or target molecule.

In another embodiment, modulators of calpain-like protease expression are identified in a method in which a cell is contacted with a candidate compound and the expression of calpain-like protease mRNA or protein in the cell is determined relative to expression of calpain-like protease mRNA or protein in a cell in the absence of the candidate compound. When expression is greater (statistically significantly greater) in the presence of the candidate compound than in its absence, the candidate compound is identified as a stimulator of calpain-like protease mRNA or protein expression. Alternatively, when expression is less (statistically significantly less) in the presence of the candidate compound than in its absence, the candidate compound is identified as an inhibitor of calpain-like protease mRNA or protein expression. The level of calpain-like protease mRNA or protein expression in the cells can be determined by methods described herein for detecting calpain-like protease mRNA or protein.

In yet another aspect of the invention, the calpain-like protease proteins can be used as "bait proteins" in a two-hybrid assay or three-hybrid assay (see, e.g. U.S. Pat. No. 5,283,317; Zervos et al. (1993) *Cell* 72:223–232; Madura et al. (1993) *J. Biol. Chem.* 268:12046–12054; Bartel et al. (1993) *Bio/Techniques* 14:920–924; Jwabuchi et al. (1993) *Oncogene* 8:1693–1696; and PCT Publication No. WO 94/10300), to identify other proteins, which bind to or interact with calpain-like protease protein ("calpain-like protease-binding proteins" or "calpain-like protease-bp") and modulate calpain-like protease activity. Such calpain-like protease-binding proteins are also likely to be involved in the propagation of signals by the calpain-like protease proteins as, for example, upstream or downstream elements of the calpain-like protease pathway.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (1) map their respective genes on a chromosome, (2) identify an individual from a minute biological sample (tissue typing); and (3) aid in forensic identification of a biological sample. These applications are described in the subsections below.

1. Chromosome Mapping

The isolated complete or partial calpain-like protease gene sequences of the invention can be used to map their respective calpain-like protease genes on a chromosome, thereby facilitating the location of gene regions associated with genetic disease. Computer analysis of calpain-like protease sequences can be used to rapidly select PCR primers (preferably 15–25 bp in length) that do not span more than one exon in the genomic DNA, thereby simplifying the amplification process. These primers can then be used for PCR screening of somatic cell hybrids containing individual human chromosomes. Only those hybrids containing the human gene corresponding to the calpain-like protease sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow (because they lack a particular enzyme), but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Bustachio et al. (1983) *Science* 220:919–924). Somatic cell hybrids containing only fragments of human chromosomes can also be produced by using human chromosomes with translocations and deletions.

Other mapping strategies that can similarly be used to map a calpain-like protease sequence to its chromosome include in situ hybridization (described in Fan et al. (1990) *Proc. Natl. Acad. Sci. USA* 87:6223–27), pre-screening with labeled flow-sorted chromosomes, and pre-selection by hybridization to chromosome specific cDNA libraries. Furthermore, fluorescence in situ hybridization (FISH) of a DNA sequence to a metaphase chromosomal spread can be used to provide a precise chromosomal location in one step. For a review of this technique, see Verma et al. (1988) *Human Chromosomes: A Manual of Basic Techniques* (Pergamon Press, NY). The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783–787.

Moreover, differences in the DNA sequences between individuals affected and unaffected with a disease associated with the calpain-like protease gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The calpain-like protease sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes and probed on a Southern blot to yield unique bands for identification. The sequences of the present invention are useful as additional DNA markers for RFLP (described in U.S. Pat. No. 5,272,057).

Furthermore, the sequences of the present invention can be used to provide an alternative technique for determining the actual base-by-base DNA sequence of selected portions of an individual's genome. Thus, the calpain-like protease sequences of the invention can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The calpain-like protease sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. The noncoding sequences of SEQ ID NO:1 can comfortably provide positive individual identification with a panel of perhaps 10 to 1,000 primers that each yield a noncoding amplified sequence of 100 bases. If a predicted coding sequence, such as that in SEQ ID NO:1 or SEQ ID NO:3, is used, a more appropriate number of primers for positive individual identification would be 500 to 2,000.

3. Use of Partial Calpain Protease Sequences in Forensic Biology

DNA-based identification techniques can also be used in forensic biology. In this manner, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" that is unique to a particular individual. As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the calpain-like protease sequences or portions thereof, e.g., fragments derived from the noncoding regions of SEQ ID NO:1 having a length of at least 20 or 30 bases.

The calpain-like protease sequences described herein can further be used to provide polynucleotide reagents, e.g., labeled or labelable probes that can be used in, for example, an in situ hybridization technique, to identify a specific tissue. This can be very useful in cases where a forensic pathologist is presented with a tissue of unknown origin. Panels of such calpain-like protease probes, can be used to identify tissue by species and/or by organ type.

In a similar fashion, these reagents, e.g., calpain-like protease primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. These applications are described in the subsections below.

1. Diagnostic Assays

One aspect of the present invention relates to diagnostic assays for detecting calpain-like protease protein and/or nucleic acid expression as well as calpain-like protease activity, in the context of a biological sample. An exemplary method for detecting the presence or absence of calpain-like protease proteins in a biological sample involves obtaining a biological sample from a test subject and contacting the biological sample with a compound or an agent capable of detecting calpain-like protease protein or nucleic acid (e.g., mRNA, genomic DNA) that encodes calpain-like protease protein such that the presence of calpain-like protease protein is detected in the biological sample. Results obtained with a biological sample from the test subject may be compared to results obtained with a biological sample from a control subject.

A preferred agent for detecting calpain-like protease mRNA or genomic DNA is a labeled nucleic acid probe capable of hybridizing to calpain-like protease mRNA or genomic DNA. The nucleic acid probe can be, for example, a full-length calpain-like protease nucleic acid, such as the nucleotide sequence of SEQ ID NO:1, a calpain-like protease coding sequence, such as the nucleotide sequence of SEQ ID NO:3, or a portion thereof, such as a nucleic acid molecule of at least 15, 30, 50, 100, 250, or 500 nucleotides in length and sufficient to specifically hybridize under stringent conditions to calpain-like protease nucleic acid molecule. Other suitable probes for use in the diagnostic assays of the invention are described herein.

A preferred agent for detecting calpain-like protease protein is an antibody capable of binding to calpain-like protease protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect calpain-like protease mRNA, protein, or genomic DNA in a biological sample in vitro as well as in vivo. For example, in vitro techniques for detection of calpain-like protease mRNA include Northern hybridizations and in situ hybridizations. In vitro techniques for detection of calpain-like protease protein include enzyme linked immunosorbent assays (ELISAs), Western blots, immunoprecipitations, and immunofluorescence. In vitro techniques for detection of calpain-like protease genomic DNA include Southern hybridizations. Furthermore, in vivo techniques for detection of calpain-like protease protein include introducing into a subject a labeled anti-calpain-like protease antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject.

The invention also encompasses kits for detecting the presence of calpain-like protease proteins in a biological sample (a test sample). Such kits can be used to determine if a subject is suffering from or is at increased risk of developing a disorder associated with aberrant expression of calpain-like protease protein (e.g., an immunological disorder). For example, the kit can comprise a labeled compound or agent capable of detecting calpain-like protease protein or mRNA in a biological sample and means for determining the amount of a calpain-like protease protein in the sample (e.g., an anti-calpain-like protease antibody or an oligonucleotide probe that binds to DNA encoding a calpain-like protease protein, e.g., SEQ ID NO:1 or SEQ ID NO:3). Kits can also include instructions for observing that the tested subject is suffering from or is at risk of developing a disorder associated with aberrant expression of calpain-like protease sequences if the amount of calpain-like protease protein or mRNA is above or below a normal level.

For antibody-based kits, the kit can comprise, for example: (1) a first antibody (e.g., attached to a solid support) that binds to calpain-like protease protein; and, optionally, (2) a second, different antibody that binds to calpain-like protease protein or the first antibody and is conjugated to a detectable agent. For oligonucleotide-based kits, the kit can comprise, for example: (1) an oligonucleotide, e.g., a detectably labeled oligonucleotide, that hybridizes to a calpain-like protease nucleic acid sequence or (2) a pair of primers useful for amplifying a calpain-like protease nucleic acid molecule.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for observing whether the tested subject is suffering from or is at risk of developing a disorder associated with aberrant expression of calpain-like protease proteins 2. Prognostic Assays The methods described herein can furthermore be utilized as diagnostic or prognostic assays to identify subjects having or at risk of developing a disease or disorder associated with calpain-like protease protein, calpain-like protease nucleic acid expression, or calpain-like protease activity. Prognostic assays can be used for prognostic or predictive purposes to thereby prophylactically treat an individual prior to the onset of a disorder characterized by or associated with calpain-like protease protein, calpain-like protease nucleic acid expression, or calpain-like protease activity.

Thus, the present invention provides a method in which a test sample is obtained from a subject, and calpain-like protease protein or nucleic acid (e.g., mRNA, genomic DNA) is detected, wherein the presence of calpain-like protease protein or nucleic acid is diagnostic for a subject having or at risk of developing a disease or disorder associated with aberrant calpain-like protease expression or activity. As used herein, a "test sample" refers to a biological sample obtained from a subject of interest. For example, a test sample can be a biological fluid (e.g., serum), cell sample, or tissue.

Furthermore, using the prognostic assays described herein, the present invention provides methods for determining whether a subject can be administered a specific agent (e.g., an agonist, antagonist, peptidomimetic, protein, peptide, nucleic acid, small molecule, or other drug candidate) or class of agents (e.g., agents of a type that decrease calpain-like protease activity) to effectively treat a disease or disorder associated with aberrant calpain-like protease expression or activity. In this manner, a test sample is obtained and calpain-like protease protein or nucleic acid is detected. The presence of calpain-like protease protein or nucleic acid is diagnostic for a subject that can be administered the agent to treat a disorder associated with aberrant calpain-like protease expression or activity.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage, a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

The methods of the invention can also be used to detect genetic lesions or mutations in a calpain-like protease gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion or mutation characterized by at least one of an alteration affecting the integrity of a gene encoding a calpain-like protease protein, or the misexpression of the calpain-like protease gene. For example, such genetic lesions or mutations can be detected by ascertaining the existence of at least one of: (1) a deletion of one or more nucleotides from a calpain-like protease gene; (2) an addition of one or more nucleotides to a calpain-like protease gene; (3) a substitution of one or more nucleotides of a calpain-like protease gene ; (4) a chromosomal rearrangement of a calpain-like protease gene; (5) an alteration in the level of a messenger RNA transcript of a calpain-like protease gene; (6) an aberrant modification of a calpain-like protease gene, such as of the methylation pattern of the genomic DNA; (7) the presence of a non-wild-type splicing pattern of a messenger RNA transcript of a calpain-like protease gene; (8) a non-wild-type level of a calpain-like protease-protein; (9) an allelic loss of a calpain-like protease gene; and (10) an inappropriate post-translational modification of a calpain-like protease protein. As described herein, there are a large number of assay techniques known in the art that can be used for detecting lesions in a calpain-like protease gene. Any cell type or tissue, in which calpain-like protease proteins are expressed may be utilized in the prognostic assays described herein.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the calpain-like protease-gene (see, e.g., Abravaya et al. (1995) *Nucleic Acids Res.* 23:675–682). It is anticipated that PCR and/or LCR may be desirable to use as a preliminary amplification step in conjunction with any of the techniques used for detecting mutations described herein.

Alternative amplification methods include self sustained sequence replication (Guatelli et al. (1990) *Proc. Natl. Acad. Sci. USA* 87:1874–1878), transcriptional amplification system (Kwoh et al. (1989) *Proc. Natl. Acad Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a calpain-like protease gene from a sample cell can be identified by alterations in restriction enzyme cleavage patterns of isolated test sample and control DNA digested with one or more restriction endonucleases. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in a calpain-like protease molecule can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2.753–759). In yet another embodiment, any of a variety of sequencing reactions known in the art can be used to directly sequence the calpain-like protease gene and detect mutations by comparing the sequence of the sample calpain-like protease gene with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the calpain-like protease gene include methods in which protection from cleavage agents is used to detect mismatched bases in RNA/RNA or RNA/DNA heteroduplexes (Myers et al. (1985) *Science* 230:1242). See, also Cotton et al. (1988) *Proc. Natl. Acad. Sci. USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more "DNA mismatch repair" enzymes that recognize mismatched base pairs in double-stranded DNA in defined systems for detecting and mapping point mutations in calpain-like protease cDNAs obtained from samples of cells. See, e.g., Hsu et al. (1994) *Carcinogenesis* 15:1657–1662. According to an exemplary embodiment, a probe based on a calpain-like protease sequence, e.g., a wild-type calpain-like protease sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in calpain-like protease genes. For example, single-strand conformation polymorphism (SSCP) may be used to detect differences in electrophoretic mobility between mutant and wild-type nucleic acids (Orita et al. (1989) *Proc. Natl. Acad. Sci. USA* 86:2766; see also Cotton (1993) *Mutat. Res.* 285:125–144; Hayashi (1992) *Genet. Anal. Tech. Appl.* 9:73–79). The sensitivity of the assay may be enhanced by using RNA (rather than DNA), in which the secondary structure is more sensitive to a change in sequence. In a preferred embodiment, the subject method utilizes heteroduplex analysis to separate double-stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc. Natl. Acad. Sci. USA* 86:6230). Such allele-specific oligonucleotides are hybridized to PCR-amplified target DNA or a number of different mutations when the oligonucleotides are attached to the hybridizing membrane and hybridized with labeled target DNA.

Alternatively, allele-specific amplification technology, which depends on selective PCR amplification, may be used in conjunction with the instant invention. Oligonucleotides used as primers for specific amplification may carry the mutation of interest in the center of the molecule so that amplification depends on differential hybridization (Gibbs et al. (1989) *Nucleic Acids Res.* 17:2437–2448) or at the extreme 3' end of one primer where, under appropriate conditions, mismatch can prevent or reduce polymerase extension (Prossner (1993) *Tibtech* 1:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnosed patients exhibiting symptoms or family history of a disease or illness involving a calpain-like protease gene.

3. Pharmacogenomics

Agents, or modulators that have a stimulatory or inhibitory effect on calpain-like protease activity (e.g., calpain-like protease gene expression) as identified by a screening assay described herein, can be administered to individuals to treat (prophylactically or therapeutically) disorders associated with aberrant calpain-like protease activity as well as to modulate the phenotype of an immune response. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of calpain-like protease protein, expression of calpain-like protease nucleic acid, or mutation content of calpain-like protease genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of calpain-like protease protein, expression of calpain-like protease nucleic acid, or mutation content of calpain-like protease genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a calpain-like protease modulator, such as a modulator identified by one of the exemplary screening assays described herein.

4. Monitoring of Effects During Clinical Trials

Monitoring the influence of agents (e.g., drugs, compounds) on the expression or activity of calpain-like protease genes (e.g., the ability to modulate aberrant cell proliferation and/or differentiation) can be applied not only in basic drug screening but also in clinical trials. For example, the effectiveness of an agent, as determined by a screening assay as described herein, to increase or decrease calpain-like protease gene expression, protein levels, or protein activity, can be monitored in clinical trials of subjects exhibiting decreased or increased calpain-like protease gene expression, protein levels, or protein activity. In such clinical trials, calpain-like protease expression or activity and preferably that of other genes that have been implicated in for example, a cellular proliferation disorder, can be used as a marker of the immune responsiveness of a particular cell.

For example, and not by way of limitation, genes that are modulated in cells by treatment with an agent (e.g., compound, drug, or small molecule) that modulates calpain-like protease activity (e.g., as identified in a screening assay described herein) can be identified. Thus, to study the effect of agents on cellular proliferation disorders, for example, in a clinical trial, cells can be isolated and RNA prepared and analyzed for the levels of expression of calpain-like protease genes and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of calpain-like protease genes or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (1) obtaining a preadministration sample from a subject prior to administration of the agent; (2) detecting the level of expression of a calpain-like protease protein, mRNA, or genomic DNA in the preadministration sample; (3) obtaining one or more postadministration samples from the subject; (4) detecting the level of expression or activity of the calpain-like protease protein, mRNA, or genomic DNA in the postadministration samples; (5) comparing the level of expression or activity of the calpain-like protease protein, mRNA, or genomic DNA in the preadministration sample with the calpain-like protease protein, mRNA, or genomic DNA in the postadministration sample or samples; and (vi) altering the administration of the agent to the subject accordingly to bring about the desired effect, i.e., for example, an increase or a decrease in the expression or activity of a calpain-like protease protein.

C. Methods of Treatment

The present invention provides for both prophylactic and therapeutic methods of treating a subject at risk of (or susceptible to) a disorder or having a disorder associated with aberrant calpain-like protease expression or activity. Additionally, the compositions of the invention find use in the treatment of disorders described herein. Thus, therapies for disorders associated with altered calpain-like protease activity are encompassed. Such disorders include, but are not limited to, disorders associated with perturbed cellular growth and differentiation; exercise-induced injury and repair; apoptosis including T-cell receptor-induced apoptosis, HIV-infected cell apoptosis, ectoposide-treated cell apoptosis, nerve growth factor deprived neuronal apoptosis; ischemia; traumatic brain injury; Alzheimer's disease and other neurodegenerative diseases; demyelinating diseases including experimental allergic encephalomyelitis (EAE) and multiple sclerosis; LGMD2A muscular dystrophy; spinal cord injury (SCI); proliferative disorders or differentiative disorders such as cancer, e.g., melanoma, prostate cancer, cervical cancer, breast cancer, colon cancer, or sarcoma; and renal cell death associated with diverse toxicants.

Further, as discussed in the exemplary section herein, the expression of the calpain-like protease has been identified in specific tissues and accordingly is related to disorders involving these tissues. Thus, methods of treatment extend to such disorders and tissues.

1. Prophylactic Methods

In one aspect, the invention provides a method for preventing in a subject a disease or condition associated with an aberrant calpain-like protease expression or activity by administering to the subject an agent that modulates calpain-like protease expression or at least one calpain-like protease gene activity. Subjects at risk for a disease that is caused, or contributed to, by aberrant calpain-like protease expression or activity can be identified by, for example, any or a combination of diagnostic or prognostic assays as described herein. Administration of a prophylactic agent can occur prior to the manifestation of symptoms characteristic of the calpain-like protease aberrancy, such that a disease or disorder is prevented or, alternatively, delayed in its progression. Depending on the type of calpain-like protease aberrancy, for example, a calpain-like protease agonist or calpain-like protease antagonist agent can be used for treating the subject. The appropriate agent can be determined based on screening assays described herein.

2. Therapeutic Methods

Another aspect of the invention pertains to methods of modulating calpain-like protease expression or activity for therapeutic purposes. The modulatory method of the invention involves contacting a cell with an agent that modulates one or more of the activities of calpain-like protease protein activity associated with the cell. An agent that modulates calpain-like protease protein activity can be an agent as described herein, such as a nucleic acid or a protein, a naturally-occurring cognate ligand of a calpain-like protease protein, a peptide, a calpain-like protease peptidomimetic, or other small molecule. In one embodiment, the agent stimulates one or more of the biological activities of calpain-like protease protein. Examples of such stimulatory agents include active calpain-like protease protein and a nucleic acid molecule encoding a calpain-like protease protein that has been introduced into the cell. In another embodiment, the agent inhibits one or more of the biological activities of calpain-like protease protein. Examples of such inhibitory agents include antisense calpain-like protease nucleic acid molecules and anti-calpain-like protease antibodies.

These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a calpain-like protease protein or nucleic acid molecule. In one embodiment, the method involves administering an agent (e.g., an agent identified by a screening assay described herein), or a combination of agents, that modulates (e.g., upregulates or downregulates) calpain-like protease expression or activity. In another embodiment, the method involves administering a calpain-like protease protein or nucleic acid molecule as therapy to compensate for reduced or aberrant calpain-like protease expression or activity.

Stimulation of calpain-like protease activity is desirable in situations in which a calpain-like protease protein is abnormally downregulated and/or in which increased calpain-like protease activity is likely to have a beneficial effect. Conversely, inhibition of calpain-like protease activity is desirable in situations in which calpain-like protease activity is abnormally upregulated and/or in which decreased calpain-like protease activity is likely to have a beneficial effect.

Other Embodiments

In another aspect, the invention features, a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a 18036, preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the 18036 nucleic acid, polypeptide, or antibody.

The capture probes can be a set of nucleic acids from a selected sample, e.g., a sample of nucleic acids derived from a control or non-stimulated tissue or cell.

The method can include contacting the 18036 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 18036. Such methods can be used to diagnose a subject, e.g., to evaluate risk for a disease or disorder, to evaluate suitability of a selected treatment for a subject, to evaluate whether a subject has a disease or disorder. 18036 is associated with calpain protease-like activity, thus it is useful for disorders associated with abnormal proteolysis.

The method can be used to detect SNPs.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express or misexpress 18036 or from a cell or subject in which a 18036 mediated response has been elicited, e.g., by contact of the cell with 18036 nucleic acid or protein, or administration to the cell or subject 18036 nucleic acid or protein; contacting the array with one or more inquiry probe, wherein an inquiry probe can be a nucleic acid, polypeptide, or antibody (which is preferably other than 18036 nucleic acid, polypeptide, or antibody); providing a two dimensional array having a plurality of addresses, each address of the plurality being positionally distinguishable from each other address of the plurality, and each address of the plurality having a unique capture probe, e.g., wherein the capture probes are from a cell or subject which does not express 18036 (or does not express as highly as in the case of the 18036 positive plurality of capture probes) or from a cell or subject which in which a 18036 mediated response has not been elicited (or has been elicited to a lesser extent than in the first sample); contacting the array with one or more inquiry probes (which is preferably other than a 18036 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing 18036, e.g., analyzing structure, function, or relatedness to other nucleic acid or amino acid sequences. The method includes: providing a 18036 nucleic acid or amino acid sequence; comparing the 18036 sequence with one or more preferably a plurality of sequences from a collection of sequences, e.g., a nucleic acid or protein sequence database; to thereby analyze 18036.

Preferred databases include GenBank™. The method can include evaluating the sequence identity between a 18036 sequence and a database sequence. The method can be performed by accessing the database at a second site, e.g., over the internet. In another aspect, the invention features, a set of oligonucleotides, useful, e.g., for identifying SNP's, or identifying specific alleles of 18036. The set includes a plurality of oligonucleotides, each of which has a different nucleotide at an interrogation position, e.g., an SNP or the site of a mutation. In a preferred embodiment, the oligonucleotides of the plurality are identical in sequence with one another (except for differences in length). The oligonucleotides can be provided with different labels, such that an oligonucleotide that hybridizes to one allele provides a signal that is distinguishable from an oligonucleotide which hybridizes to a second allele.

This invention is further illustrated by the following examples which should not be construed as limiting.

EXAMPLES

Example 1

Identification and Characterization of Human 18036 cDNAs

The human 18036 sequence (FIGS. 1A–B; SEQ ID NO:1), which is approximately 2180 nucleotides long including untranslated regions, contains a predicted methionine-initiated coding sequence of about 1554 nucleotides (nucleotides 183–1737 of SEQ ID NO:1; SEQ ID NO:3). The coding sequence encodes a 517 amino acid protein (SEQ ID NO:2).

PFAM analysis indicates that the 18036 polypeptide shares a high degree of sequence similarity with the calpain family of cysteine proteases. For general information regarding PFAM identifiers, PS prefix and PF prefix domain identification numbers, refer to Sonnhammer et al. (1997) Protein 28:405–420 and http//www.psc.edu/general/software/packages/pfam/pfam.html.

As used herein, the term "calpain domain" includes an amino acid sequence of about 200–400 amino acid residues in length and having a bit score for the alignment of the sequence to the calpain cysteine protease domain (HMM) of at least 8. Preferably, a calpain domain includes at least about 250–350 amino acids, more preferably about 275–325 amino acid residues, or about 300–320 amino acids and has a bit score for the alignment of the sequence to the calpain domain (HMM) of at least 16 or greater. The calpain domain (HMM) has been assigned the PFAM Accession PF00648 (http://pfam.wustl.edu/). An alignment of the calpain domain (amino acids 13–322 of SEQ ID NO:2) of human 18036 with a consensus amino acid sequence derived from a hidden Markov model is depicted in FIG. 7.

In a preferred embodiment a calpain protease-like polypeptide or protein has a "calpain domain" or a region which includes at least about 200–400 more preferably about 250–350 or 285–325 amino acid residues and has at least about 60%, 70%, 80%, 90%, 95%, 96%, 97%, 98%, 99%, or 100% sequence identity with an "calpain domain," e.g., the calpain domain of human 18036 (e.g., amino acid residues 13–322 of SEQ ID NO:2).

To identify the presence of a "calpain" domain in a calpain-like protease protein sequence, and make the determination that a polypeptide or protein of interest has a particular profile, the amino acid sequence of the protein can be searched against a database of HMMs (e.g., the Pfam database, release 2.1) using the default parameters (http://www.sanger.ac.uk/Software/Pfam/HMM_search). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) Proteins 28(3):405–420 and a detailed description of HMMs can be found, for example, in Gribskov et al. (1990) Meth. Enzymol. 183:146–159; Gribskov et al. (1987) Proc. Natl. Acad. Sci. USA 84:4355–4358; Krogh et al. (1994) J. Mol. Biol. 235:1501–1531; and Stultz et al. (1993) Protein Sci. 2:305–314, the contents of which are incorporated herein by reference.

Pfam analysis also detected a calpain large subunit domain (PFAM Accession No. PF01067) from amino acids 338–490 of SEQ ID NO:2. SMART analysis detected a cysteine protease domain from amino acids 7 to 329 of SEQ ID NO:2. ProDom analysis detected a calpain domain (ProDom Accession No. PD002154) from amino acids 13 to 295 of SEQ ID NO:2. The alignment of this segment of the 18036 amino acid sequence with the ProDom calpain domain is shown in FIG. 8. ProDom analysis also detected a calpain domain from amino acids 344–487 of SEQ ID NO:2.

Example 2

Tissue Distribution of 18036 mRNA

Expression levels of 18036 in various tissue and cell types were determined by quantitative RT-PCR (Reverse Transcriptase Polymerase Chain Reaction; Taqman® brand PCR kit, Applied Biosystems). The quantitative RT-PCR reactions were performed according to the kit manufacturer's instructions. The results indicated that 18036 is expressed in the following human tissues and cell types (FIG. 6 and data not shown): aorta, brain (including brain cortex and glial cells), breast, cervix, colon, esophagus, heart, kidney, liver, lung, lymph node, muscle, ovary, placenta, prostate, small intestine, spleen, testes, thymus, thyroid, and vein (including umbilical vein endothelial cells grown under static or shear force conditions). TaqMan® 18036 expression in normal and hepatitis B virus-infected human liver tissue and liver cell lines is shown in FIG. 9

Northern blot hybridizations with various RNA samples are performed under standard. conditions and washed under stringent conditions, i.e., 0.2xSSC at 65° C. A DNA probe corresponding to all or a portion of the 18036 cDNA (SEQ ID NO:1 or SEQ ID NO:3) can be used. The DNA is radioactively labeled with 32P-dCTP using the Prime-It® brand Kit (Stratagene, La Jolla, Calif.) according to the instructions of the supplier. Filters containing mRNA from mouse hematopoietic and endocrine tissues, and cancer cell lines (Clontech, Palo Alto, Calif.) are probed in ExpressHyb™ brand hybridization solution (Clontech) and washed at high stringency according to manufacturer's recommendations.

Example 3

Recombinant Expression of 18036 in Bacterial Cells

In this example, 18036 is expressed as a recombinant glutathione-S-transferase (GST) fusion polypeptide in *E. coli* and the fusion polypeptide is isolated and characterized. Specifically, 18036 is fused to GST and this fusion polypeptide is expressed in *E. coli*, e.g., strain PEB199. Expression of the GST-18036 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 4

Expression of Recombinant 18036 Protein in COS Cells

To express the 18036 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 18036 protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the 18036 DNA sequence is amplified by PCR using two primers. The 5' primer contains the restriction site of interest followed by approximately twenty nucleotides of the 18036 coding sequence starting from the initiation codon; the 3' end sequence contains complementary sequences to the other restriction site of interest, a translation stop codon, the HA tag or FLAG tag and the last 20 nucleotides of the 18036 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 18036 gene is inserted in the correct orientation. The ligation mixture is transformed into *E. coli* cells (strains HB101, DH5α™, SURE®, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 18036-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989. The expression of the 18036 polypeptide is detected by radiolabelling (35S-methionine or 35S-cysteine available from NEN, Boston, Mass., can be used) and immunoprecipitation (Harlow, E. and Lane, D. Antibodies: A Laboratory Manual, Cold Spring Harbor Laboratory Press, Cold Spring Harbor, N.Y., 1988) using an HA specific monoclonal antibody. Briefly, the cells are labeled for 8 hours with 35S-methionine (or 35S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 18036 coding sequence is cloned directly into the polylinker of the pCDNA/Amp vector using the appropriate restriction sites. The resulting plasmid is transfected into COS cells in the manner described above, and the expression of the 18036 polypeptide is detected by radiolabelling and immunoprecipitation using a 18036 specific monoclonal antibody.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Those skilled in the art will recognize, or be able to ascertain using no more than routine experimentation, many equivalents to the specific embodiments of the invention described herein. Such equivalents are intended to be encompassed by the following claims.

That which is claimed:

1. An isolated nucleic acid molecule comprising a nucleotide sequence selected from the group consisting of:

a) a nucleotide sequence having at least 95% sequence identity with the nucleotide sequence set forth in SEQ ID NO:1, wherein said nucleotide sequence encodes a polypeptide having calpain protease activity;

b) the nucleotide sequence set forth in SEQ ID NO:3;

c) a nucleotide sequence having at least 95% sequence identity with the nucleotide sequence of the h18036 cDNA insert of the plasmid deposited with the ATCC as Patent Deposit Number PTA-2203, wherein said nucleotide sequence encodes a polypeptide having calpain protease activity;

d) the nucleotide sequence of a fragment of the nucleotide sequence set forth in SEQ ID NO:1, wherein said fragment consists of at least 1200 contiguous nucleotides of the nucleotide sequence set forth in SEQ ID NO:1 and said nucleotide sequence of a fragment of the nucleotide sequence set forth in SEQ ID NO:1 encodes a polypeptide having calpain protease activity;

e) the nucleotide sequence of a fragment of the nucleotide sequence set forth in SEQ ID NO:3, wherein said fragment consists of at least 1200 contiguous nucleotides of the nucleotide sequence set forth in SEQ ID NO:3 and said nucleotide sequence of a fragment of the nucleotide sequence set forth in SEQ ID NO:3 encodes a polypeptide having calpain protease activity;

f) the nucleotide sequence of a fragment of the nucleotide sequence of the h18036 cDNA insert of the plasmid deposited with the ATCC as Patent Deposit Number PTA-2203, wherein said fragment consists of at least 1200 contiguous nucleotides of the nucleotide sequence of the h18036 cDNA insert of the plasmid deposited with the ATCC as Patent Deposit Number PTA-2203 and said nucleotide sequence of a fragment of the nucleotide sequence of the h18036 cDNA insert of the plasmid deposited with the ATCC as Patent Deposit Number PTA-2203 encodes a polypeptide having calpain protease activity;

g) a nucleotide sequence encoding the amino acid sequence set forth in SEQ ID NO:2;

h) a nucleotide sequence encoding the amino acid sequence encoded by the h18036 cDNA insert of the plasmid deposited with the ATCC as Patent Deposit Number PTA-2203;

i) a nucleotide sequence encoding a fragment of the amino acid sequence set forth in SEQ ID NO:2, wherein said fragment has calpain protease activity and consists of at least 400 contiguous amino acids of SEQ ID NO:2, j) a nucleotide sequence encoding a fragment of the amino acid sequence encoded by the h18036 cDNA insert of the plasmid deposited with the ATCC as Patent Deposit Number PTA-2203, wherein the fragment has calpain protease activity and consists of at least 400 contiguous amino acids of the amino acid sequence encoded by the h18036 cDNA insert of the plasmid deposited with the ATCC as Patent Deposit Number PTA-2203; and k) a nucleotide sequence fully complementary to the nucleotide sequences of a), b), c), d), e), f), g), h), i), or j).

2. The isolated nucleic acid molecule of claim 1, wherein said nucleic acid molecule comprises a nucleotide sequence selected from the group consisting of:

a) the nucleotide sequence set forth in SEQ ID NO:1;

b) the nucleotide sequence set forth in SEQ ID NO:3;

c) a nucleotide sequence encoding the amino acid sequence set forth in SEQ ID NO:2; and d) a nucleotide sequence fully complementary to the nucleotide sequences of a), b), or c).

3. The isolated nucleic acid molecule of claim 1, wherein said nucleic acid molecule comprises a nucleotide sequence selected from the group consisting of:
   a) the nucleotide sequence of the h18036 cDNA insert of the plasmid deposited with ATCC as Patent Deposit Number PTA-2203;
   b) a nucleotide sequence encoding the amino acid sequence encoded by the h18036 cDNA insert of the plasmid deposited with the ATCC as Patent Deposit Number PTA-2203; and
   c) a nucleotide sequence fully complementary to the nucleotide sequences of a) or b).

4. The isolated nucleic acid molecule of claim 1, wherein said nucleic acid molecule comprises a nucleotide sequence selected from the group consisting of:
   a) a nucleotide sequence having at least 98% sequence identity with the nucleotide sequence set forth in SEQ ID NO:1, wherein said nucleotide sequence encodes a polypeptide having calpain protease activity; and
   b) a nucleotide sequence fully complementary to the nucleotide sequence of a).

5. A vector comprising the nucleic acid molecule of claim 1.

6. The nucleic acid molecule of claim 1 further comprising a nucleotide sequence encoding a heterologous polypeptide.

7. A host cell which contains the nucleic acid molecule of claim 5.

8. The host cell of claim 7 wherein said host cell is a mammalian host cell.

9. A non-human mammalian host cell containing the nucleic acid molecule of claim 1.

10. A vector comprising the nucleic acid molecule of claim 2.

11. The nucleic acid molecule of claim 2 further comprising a nucleotide sequence encoding a heterologous polypeptide.

12. A host cell which contains the nucleic acid molecule of claim 10.

13. The host cell of claim 12 wherein said host cell is a mammalian host cell.

14. A non-human mammalian host cell containing the nucleic acid molecule of claim 2.

15. A method for producing a polypeptide comprising an amino acid sequence selected from the group consisting of:
   a) the amino acid sequence set forth in SEQ ID NO:2;
   b) the amino acid sequence encoded by the h18036 cDNA insert of the plasmid deposited with the ATCC as Patent Deposit Number PTA-2203;
   c) the amino acid sequence of a fragment of the amino acid sequence set forth in SEQ ID NO:2, wherein said fragment has calpain protease activity and consists of at least 400 contiguous amino acids of the amino acid sequence set forth in SEQ ID NO:2, and
   d) the amino acid sequence of a fragment of the amino acid sequence encoded by the h18036 cDNA insert of the plasmid deposited with the ATCC as Patent Deposit Number PTA-2203, wherein said fragment has calpain protease activity and consists of at least 400 contiguous amino acids of the amino acid sequence encoded by the h18036 cDNA insert of the plasmid deposited with the ATCC as Patent Deposit Number PTA-2203;
   said method comprising culturing a host cell containing a nucleic acid molecule encoding said polypeptide under conditions such that the nucleic acid molecule is expressed.

16. The method of claim 15, wherein said polypeptide comprises the amino acid sequence set forth in SEQ ID NO:2.

17. The method of claim 15, wherein said polypeptide comprises the amino acid sequence encoded by the cDNA insert of the plasmid deposited with the ATCC as Patent Deposit Number PTA-2203.

18. A kit for use in a method of detecting the presence of a nucleic acid molecule of claim 1, said kit comprising a nucleic acid probe and instructions for use, wherein said nucleic acid probe is selected from the group consisting of:
   a) a nucleic acid molecule having at least 95% sequence identity with the nucleotide sequence set forth in SEQ ID NO:1, wherein said nucleotide sequence encodes a polypeptide having calpain protease activity;
   b) the nucleic acid molecule set forth in SEQ ID NO:3;
   c) a nucleic acid molecule having at least 95% sequence identity with the nucleotide sequence of the h18036 cDNA insert of the plasmid deposited with the ATCC as Patent Deposit Number PTA-2203, wherein said nucleic acid molecule encodes a polypeptide having calpain protease activity;
   d) a fragment of the nucleotide sequence set forth in SEQ ID NO:1, wherein said fragment consists of at least 1200 contiguous nucleotides of the nucleotide sequence set forth in SEQ ID NO:1 and said fragment of the nucleotide sequence set forth in SEQ ID NO:1 encodes a polypeptide having calpain protease activity;
   e) a fragment of the nucleotide sequence set forth in SEQ ID NO:3, wherein said fragment consists of at least 1200 contiguous nucleotides of the nucleotide sequence set forth in SEQ ID NO:3 and said fragment of the nucleotide sequence set forth in SEQ ID NO:3 encodes a polypeptide having calpain protease activity;
   f) a fragment of the nucleotide sequence of the h18036 cDNA insert of the plasmid deposited with the ATCC as Patent Deposit Number PTA-2203, wherein said fragment consists of at least 1200 contiguous nucleotides of the nucleotide sequence of the h18036 cDNA insert of the plasmid deposited with the ATCC as Patent Deposit Number PTA-2203 and said fragment of the nucleotide sequence of the h18036 cDNA insert of the plasmid deposited with the ATCC as Patent Deposit Number PTA-2203 encodes a polypeptide having calpain protease activity;
   g) a nucleic acid molecule encoding the amino acid sequence set forth in SEQ ID NO:2;
   h) a nucleic acid molecule encoding the amino acid sequence encoded by the h18036 cDNA insert of the plasmid deposited with the ATCC as Patent Deposit Number PTA-2203;
   i) a nucleic acid molecule encoding a fragment of the amino acid sequence set forth in SEQ ID NO:2, wherein said fragment has calpain protease activity and consists of at least 400 contiguous amino acids of SEQ ID NO:2;
   j) a nucleic acid molecule encoding a fragment of the amino acid sequence encoded by the h18036 cDNA insert of the plasmid deposited with the ATCC as Patent Deposit Number PTA-2203, wherein the fragment has calpain protease activity and consists of at least 400 contiguous amino acids of the amino acid sequence encoded by the h18036 cDNA insert of the plasmid deposited with the ATCC as Patent Deposit Number PTA-2203; and
   k) a nucleotide sequence fully complementary to the nucleotide sequences of a), b), c), d), e), f), g), h), i), or j).

* * * * *